United States Patent
Hertz et al.

(10) Patent No.: US 10,603,392 B2
(45) Date of Patent: Mar. 31, 2020

(54) DIALYSIS MONITORS AND METHODS OF OPERATION

(71) Applicant: GAMBRO LUNDIA AB, Lund (SE)

(72) Inventors: Thomas Hertz, Lund (SE); Sture Hobro, Lund (SE); Lennart Jönsson, Bjärred (SE)

(73) Assignee: GAMBRO LUNDIA AB, Lund (SE)

( * ) Notice: Subject to any disclaimer, the term of this patent is extended or adjusted under 35 U.S.C. 154(b) by 311 days.

(21) Appl. No.: 15/030,531

(22) PCT Filed: Nov. 11, 2014

(86) PCT No.: PCT/EP2014/074236
§ 371 (c)(1),
(2) Date: Apr. 19, 2016

(87) PCT Pub. No.: WO2015/071244
PCT Pub. Date: May 21, 2015

(65) Prior Publication Data
US 2016/0256582 A1    Sep. 8, 2016

(30) Foreign Application Priority Data

Nov. 13, 2013 (SE) ........................ 1351340

(51) Int. Cl.
*A61L 2/04* (2006.01)
*A61M 1/16* (2006.01)
*A61L 2/24* (2006.01)

(52) U.S. Cl.
CPC ............ *A61L 2/04* (2013.01); *A61L 2/24* (2013.01); *A61M 1/1686* (2013.01); *A61M 1/1688* (2014.02); *A61M 2205/3626* (2013.01)

(58) Field of Classification Search
CPC ....................................................... A61L 2/04
See application file for complete search history.

(56) References Cited

U.S. PATENT DOCUMENTS 3,809,241 A   5/1974  Alvine
4,018,684 A   4/1977  Uffer
(Continued)

FOREIGN PATENT DOCUMENTS

DE   2934167   3/1981
DE   3416955   11/1985
(Continued)

OTHER PUBLICATIONS

Search Report for International Patent Application PCT/EP2014/074236 dated Jan. 21, 2015 (4 pages).
(Continued)

*Primary Examiner* — Donald R Spamer
(74) *Attorney, Agent, or Firm* — K&L Gates LLP

(57) ABSTRACT

Dialysis monitors capable of storing and using thermal energy and methods related thereto are disclosed. Dialysis monitors capable of storing and using disinfection and/or cleaning fluids which was used at an earlier disinfection and/or cleaning event and methods related thereto are also disclosed. Thermally stored energy may, for example, be used for quick thermal disinfection of the fluid path, quick start-up of the preparation of treatment fluid, and as back-up power for continuous preparation of treatment fluid should externally provided power be interrupted.

25 Claims, 6 Drawing Sheets

(56) References Cited

U.S. PATENT DOCUMENTS

| | | | |
|---|---|---|---|
| 4,163,554 A | 8/1979 | Bernhardt | |
| 4,683,053 A | 7/1987 | Polaschegg | |
| 4,789,467 A | 12/1988 | Linsday et al. | |
| 5,591,344 A | 1/1997 | Kenley et al. | |
| 5,895,578 A | 4/1999 | Simard et al. | |
| 5,948,247 A * | 9/1999 | Gillerfalk | A61M 1/1688 210/175 |
| 6,051,188 A | 4/2000 | Spickermann et al. | |
| 6,251,279 B1 | 6/2001 | Peterson et al. | |
| 6,579,494 B1 | 6/2003 | Chevallet et al. | |
| 2004/0079700 A1 | 4/2004 | Wood et al. | |
| 2004/0215129 A1 | 10/2004 | Edgson et al. | |
| 2005/0171501 A1 | 8/2005 | Kelly | |
| 2006/0291839 A1 | 12/2006 | Yano | |
| 2007/0102357 A1 | 5/2007 | Weatherill | |
| 2009/0134080 A1 | 5/2009 | Fabig | |
| 2009/0206017 A1 | 8/2009 | Rohde et al. | |
| 2011/0192796 A1 | 8/2011 | Smejtek et al. | |
| 2012/0308431 A1 | 12/2012 | Kotsos et al. | |
| 2013/0313902 A1 * | 11/2013 | Sako | H02J 9/005 307/23 |
| 2014/0098627 A1 | 4/2014 | Mochizuki et al. | |

FOREIGN PATENT DOCUMENTS

| | | |
|---|---|---|
| DE | 3447989 | 1/1986 |
| DE | 10013964 | 9/2001 |
| DE | 10310418 | 9/2004 |
| DE | 19655227 | 8/2009 |
| EP | 0428009 | 5/1991 |
| EP | 1236685 | 9/2002 |
| JP | S6129361 | 2/1986 |
| JP | 2003180825 | 7/2003 |
| JP | 2004049977 | 2/2004 |
| JP | 2008023325 | 2/2008 |
| JP | 2009000237 | 1/2009 |
| JP | 2009056271 | 3/2009 |
| JP | 2010194092 | 9/2010 |
| JP | 2010279423 | 12/2010 |
| WO | 9609080 | 3/1996 |
| WO | 9640313 | 12/1996 |
| WO | 0057935 | 10/2000 |
| WO | 0057928 | 10/2001 |
| WO | 2012119799 | 9/2012 |
| WO | 2012166377 | 12/2012 |

OTHER PUBLICATIONS

Written Opinion for International Patent Application PCT/EP2014/074236 dated Jan. 21, 2015 (6 pages).
International Search Report PCT/EP2014/078401—dated Apr. 1, 2015—3 pages.
Written Opinion of the International Searching Authority PCT/EP2014/078401—dated Apr. 1, 2015—8 pages.
International Search Report and Written Opinion dated Feb. 4, 2014, for related International Appln. No. PCT/EP2013/073705 (12 pages).
Rosenberg, "Thermal Disinfection—The A0 Concept and the Biological Background", Central Sterilisation, 2003, vol. 11, pp. 118-120.
Japanese Office Action issued in related Japanese Patent Application No. 2016-530833 dated Jun. 6, 2018. 9 pages.

* cited by examiner

DIALYSIS MONITORS AND METHODS OF OPERATION

PRIORITY CLAIM

The present application is a National Phase of International Application No. PCT/EP2014/074236, filed on Nov. 11, 2014, which claims priority to Swedish Patent Application No. 1351340-3, filed Nov. 13, 2013, the entire contents of each of which are incorporated herein by reference and relied upon.

TECHNICAL FIELD

The present invention relates to dialysis monitors capable of storing and using thermal energy and methods related thereto.

The thermally stored energy may, for example, be used for quick thermal disinfection of the fluid path, quick start-up of the preparation of treatment fluid, and as back-up power for continuous preparation of treatment fluid should externally provided power be interrupted.

The present invention also relates to dialysis monitors capable of storing and using disinfection and/or cleaning fluids which was used at an earlier disinfection and/or cleaning event and methods related thereto.

BACKGROUND

There are several types of treatments in which blood is extracted in an extracorporeal blood circuit. Such treatments involve, for example, haemodialysis, haemofiltration, haemodiafiltration, plasmapheresis, etc. Normally, blood is removed from a blood vessel at an access site and returned to the same blood vessel or at another location in the body.

In for example the cases of haemodialysis, haemofiltration, haemodiafiltration, and plasmapheres, but not limited to these cases, a treatment fluid (also referred to as a dialysis fluid) is made approximately isotonic with a patient's blood. The treatment fluid and the patient's blood are made to flow on each side of a semi-permeable membrane of a membrane device (referred to as a dialyzer). Diffusive transfer is achieved from one side of the membrane to the other when the concentration of the substance on each side of the membrane differs. Such substances may be impurities in the blood (urea, creatinine, etc.) which thereby migrates from the blood to the treatment fluid. Since fluid normally has to be removed from the patient during haemodialysis, a convective transfer by ultrafiltration, resulting from a pressure difference created between the blood side and the treatment fluid side of the membrane, is added to the diffusive transfer.

An apparatus for extracorporeal blood treatment includes a treatment control monitor (dialysis monitor) which is connected to a disposable extracorporeal blood circuit. The disposable extracorporeal blood circuit includes blood transport lines (in general an arterial line for blood removal from the patient, and a venous line for blood return to the patient) and the membrane device for blood treatment.

The semi-permeable membrane of the membrane device divides a blood compartment, connected to the blood transport lines, and a fluid compartment, connected to treatment fluid supply and discharge circuits. The blood transport lines are further coupled to a sensor and actuator system equipped on the treatment control monitor, which system normally comprises means for blood circulation, pressure sensors, air bubble sensor, one or more circuit blocking clamps, blood detector, etc.

The treatment fluid supply circuit receives purified water from a water supply system. The water supply system may be a small unit providing water to only a single treatment control monitor but may also be a large unit providing water by means of a water system loop arrangement to a significant number of treatment units in for example a hospital or a clinic.

Dialysis fluid, which may come into contact with the patients' blood, is often prepared from the purified water by means of a treatment fluid supply circuit. It is of paramount importance that the dialysis fluid used for the treatment is free from virus, fungi, bacteria and their residue and degradation products, such as endotoxins.

Therefore, the treatment fluid path of a dialysis monitor may be disinfected between dialysis treatments in order to reduce the presence of virus, fungi, bacteria, etc. in the treatment fluid path. Chemical disinfection (e.g. using NaOCl or other chemical disinfection agents) is an efficient way to reduce the presence of bacteria, etc. but it makes great demands on the following rinse procedure and requires very close measuring to assure that the treatment fluid path is free of chemical residual products before being used for subsequent treatments. The chemical process is not environmentally friendly and may have a negative effect on the life-length of the disinfected parts and components.

In an alternative disinfection process, thermal disinfection is achieved by letting hot water pass through the treatment fluid path. As a result, the problem of chemical residual products does not exist, the process puts less load on the environment, and has comparatively less negative effect on the life-length of the disinfected parts and components.

In a further alternative disinfection process, the thermal disinfection is combined with chemical agents, such as citric acid, in order to achieve an efficient disinfection of the treatment fluid path.

Thermal disinfection of the treatment fluid path of a monitor is preferably carried out after the treatment of each patient. As the number of dialysis patients increases there is a need to increase the available time for treatments in the clinics. Consequently, there is a desire to reduce the time spent on disinfection between treatments.

Before dialysis treatment can be commenced for a patient, the dialysis monitor needs a certain time to start up the production of treatment fluid with the correct composition and at a set temperature. Again, as the number of dialysis patients increases there is a need to increase the available time for treatments in the clinics. Consequently, there is a need to reduce the time spent on the starting-up of the preparation of the treatment fluid before the dialysis treatment can be commenced on the patient.

An interruption of externally provided electrical power normally leads to an interruption of an on-going dialysis treatment. This is also true even if the duration of the interruption of power is short. This result is that patients, nurses and other staff of clinics and hospitals have to interrupt on-going treatments, return blood present in the extracorporeal blood circuit to the patient, wait for power to return, and either re-start dialysis treatment on the same patient or reschedule the patient to a new available time-slot for treatment. Consequently, there is a need to reduce the impact of interruption of externally provided electrical power for patients and care-givers.

SUMMARY

According to an aspect of the present invention, there is provided a dialysis monitor having a treatment fluid path configured to provide treatment fluid at a first temperature to a dialyzer while dialysis treatment is being performed by the dialysis monitor. The dialysis monitor further comprises a controller and a tank which is connected to the treatment fluid path. The tank is configured to hold a fluid having a temperature higher than the first temperature. Furthermore, the controller is programmed to arrange that the tank holds the fluid having the higher temperature at least for a period of time while the treatment fluid path is supplying treatment fluid at the first temperature during a dialysis treatment.

According to another aspect of the present invention, the dialysis monitor is further configured to discharge the fluid held in the tank at a time when dialysis treatment is not being performed in order to perform thermal disinfection of the treatment fluid path.

According to another aspect of the present invention, the dialysis monitor is further configured to convey fluid from the tank in order to provide treatment fluid substantially at the first temperature.

According to another aspect of the present invention, the dialysis monitor is further configured to detect whether externally provided electrical power to the dialysis monitor is interrupted. The dialysis monitor is configured to convey fluid from the tank at a time when the controller has detected that externally electrical power to the dialysis monitor has been interrupted.

According to another aspect of the present invention, the dialysis monitor is further configured to convey fluid from the tank at a time when the dialysis monitor is starting up the preparation of treatment fluid.

According to another aspect of the present invention, there is provided a method of thermally disinfecting a treatment fluid path of a dialysis monitor at a time when dialysis treatment is not being performed. The dialysis monitor is configured to use treatment fluid at a first temperature while dialysis treatment is being performed. The method comprises the step of discharging a preheated fluid from a tank of the dialysis monitor so as to thermally disinfect the treatment fluid path, the discharged fluid having a temperature which is higher than the first temperature, and wherein the discharged fluid was held at a temperature higher than the first temperature at least for a period of time while dialysis treatment was being performed.

According to another aspect of the present invention, there is provided a method of heating treatment fluid of a dialysis monitor. The dialysis monitor is configured to use treatment fluid at a first temperature while dialysis treatment is being performed and the dialysis monitor comprises a tank. The method comprises the step of conveying a preheated fluid from the tank of the dialysis monitor so as to heat the treatment fluid, the preheated fluid having a temperature which is higher than the first temperature, and wherein the conveyed fluid was held at a temperature higher than the first temperature at least for a period of time while dialysis treatment was being performed.

According to another aspect of the present invention, there is provided a dialysis monitor which comprises a treatment fluid path configured to provide treatment fluid to a dialyzer while dialysis treatment is being performed by the dialysis monitor, a controller, and a tank connected to the treatment fluid path. The dialysis monitor is configured to perform disinfection and/or cleaning of at least a portion of the treatment fluid path by means of a disinfection and/or cleaning fluid at a first disinfection and/or cleaning event. The dialysis monitor is further configured to store at least a portion of the disinfection and/or cleaning fluid in the tank at the end of or after the first disinfection and/or cleaning event, and the dialysis monitor is configured to discharge at least a portion of the stored disinfection and/or cleaning fluid into at least of a portion of the treatment fluid path at a subsequent disinfection and/or cleaning event.

According to another aspect of the present invention, there is provided a method of disinfecting and/or cleaning at least a portion of a treatment fluid path of a dialysis monitor at first and subsequent events when dialysis treatment is not being performed. The method comprises the steps of disinfecting and/or cleaning at least a portion of the treatment fluid path at the first disinfection and/or cleaning event by means of a disinfection and/or cleaning fluid, and storing at least a portion of the disinfection and/or cleaning fluid in a tank at the end of or after the first disinfection and/or cleaning event, and discharging at least a portion of the stored disinfection and/or cleaning fluid into at least of a portion of the treatment fluid path at a subsequent disinfection and/or cleaning event.

An advantage, at least in respect of some embodiments of the present invention, is that thermal disinfection of the Dialysis Monitor can be achieved in a short period of time, thereby making the time-between-treatments shorter. This is achieved by the arrangement that the tank holds the fluid having a higher temperature at least for a period of time while the treatment fluid path is supplying treatment fluid at the first temperature during a dialysis treatment. There is thereby no or less need to perform time-consuming heating of the fluid to be used for thermal disinfection after dialysis treatment and before thermal disinfection can take place— the fluid in the tank is already at an elevated temperature when being discharged from the tank.

Another advantage, at least in respect of some embodiments of the present invention, is that the time spent on the starting-up of the preparation of the treatment fluid before the dialysis treatment can be commenced on the patient can be shortened. This is achieved by the arrangement that fluid having a higher temperature than the first temperature, that is the temperature of the treatment fluid while dialysis treatment is being performed, is conveyed from the tank in order to provide treatment fluid substantially at the first temperature. Consequently, there is an advantage of a more efficient use of the Dialysis Monitors (e.g. measured in percentage of time available for dialysis treatment of patients at for example clinics and hospitals). The working hours of the operating staff (nurses and technicians, as the case may be, who operate the Dialysis Monitors) can be shortened which in turn has positive economic effects for the clinics/hospitals and also positive work environmental effects for the operating staff. Patients also benefit as the Dialysis Monitors are used more efficiently.

Another advantage, at least in respect of some embodiments of the present invention, is that impact of interruption in externally provided electrical power for patients and care-givers can be reduced. This is achieved by the arrangement that fluid having a higher temperature than the first temperature, that is the temperature of the treatment fluid while dialysis treatment is being performed, is conveyed from the tank in order to provide treatment fluid substantially at the first temperature at a time when the dialysis monitor has detected that externally provided electrical power to the dialysis monitor has been interrupted.

Another advantage, at least in respect of some embodiments of the present invention, is that disinfection and/or cleaning fluids which was used at an earlier disinfection and/or cleaning event can be re-used. This is achieved by the arrangement that disinfection and/or cleaning fluid is stored in the tank at the end of or after a first disinfection and/or cleaning event, and that at least a portion of the stored disinfection and/or cleaning fluid is discharged into at least of a portion of the treatment fluid path at a subsequent disinfection and/or cleaning event.

DETAILED DESCRIPTION

Figure 1:
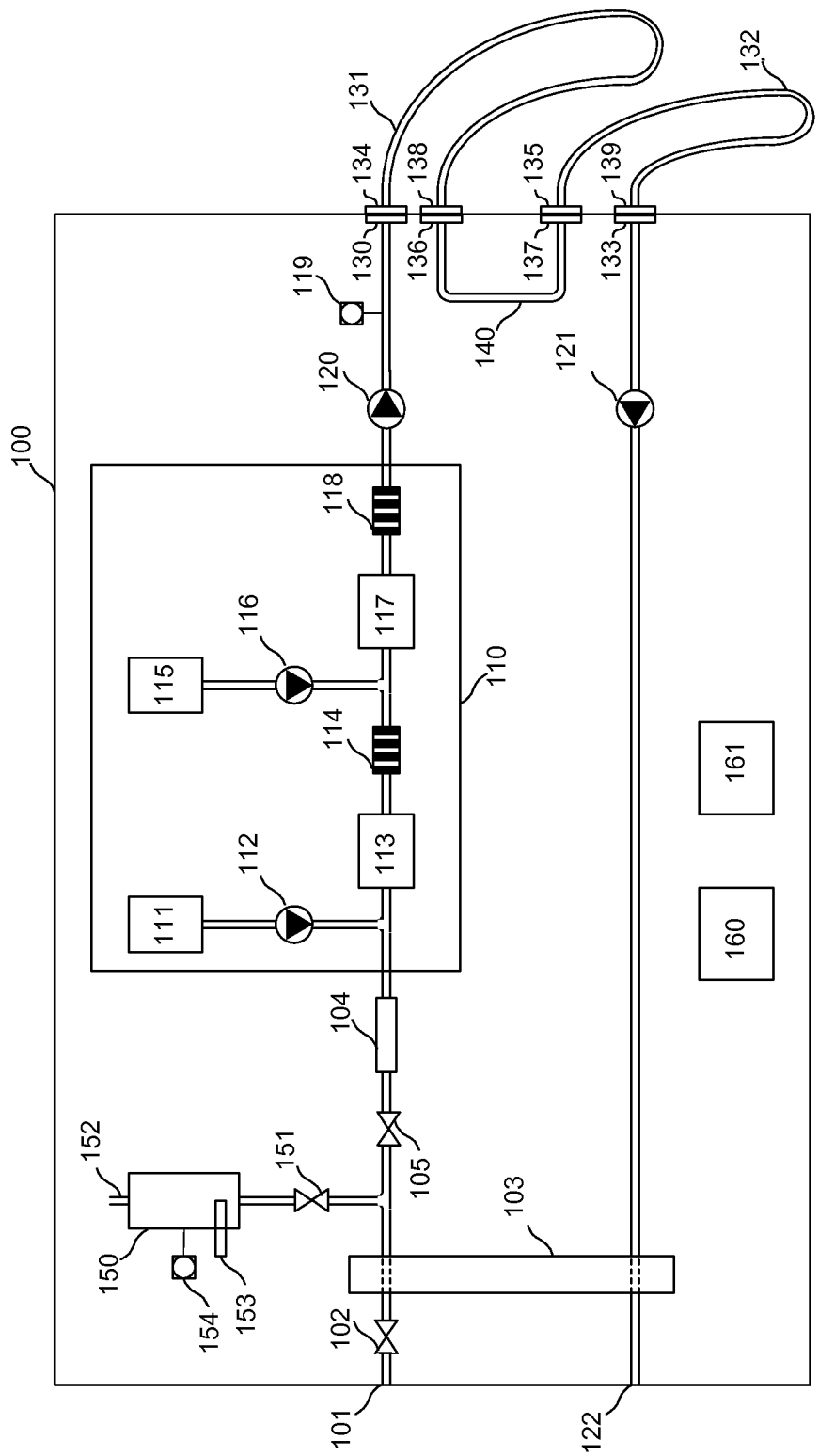
FIG. 1 shows a schematic diagram of a portion of a dialysis monitor according to an embodiment of the present invention.

FIG. 1 shows a schematic diagram of a portion of a Dialysis Monitor 100 according to an embodiment of the present invention. The schematic diagram mainly shows elements of the Treatment Fluid Path of the Dialysis Monitor. The upstream portion of the Treatment Fluid Path starts at an Inlet 101 which is configured/adapted for receiving purified water supplied to the dialysis monitor from a water supply system (not shown). The Inlet is connected to an Inlet Valve 102 which in turn connects to the inlet on the first side of a Heat Exchanger 103. The outlet on the first side of the Heat Exchanger connects to inlet of a Treatment Fluid Path Heater 104, which is configured to heat fluid present in the Treatment Fluid Path within and/or in the vicinity of the Treatment Fluid Path Heater. The outlet of the Treatment Fluid Path Heater is connected to an inlet of a Treatment Fluid Preparation Unit 110.

The Treatment Fluid Preparation Unit 110, in operation, prepares the treatment fluid to be used during the dialysis treatment. As mentioned above, the treatment fluid is made approximately isotonic with a patient's blood and is used to circulate on one side of a semi-permeable membrane (not shown) of a membrane device referred to as a dialyzer (not shown). During treatment, the patient's blood is made to flow on the other side of the semi-permeable membrane of the dialyzer. The treatment fluid may additionally be used as a substitute fluid, or in the preparation of a substitute fluid, in certain treatment methods such as haemodiafiltration where substitute fluid is infused into the blood line before and/or after the dialyzer.

In the embodiment shown in FIG. 1, the treatment fluid is prepared from the A-concentrate which comprises all electrolytes except bicarbonate and the B-concentrate which comprises bicarbonate. The A-Concentrate Container 111, which comprises the A-concentrate, is connected to an inlet of an A-Pump 112. The outlet of the A-Pump is connected to the Treatment Fluid Path between the Treatment Fluid Path Heater outlet and an inlet of a First Mixing Chamber 113. The outlet of the First Mixing Chamber is connected to an inlet of a First Conductivity Cell 114. The B-Concentrate Container 115, which comprises the B-concentrate, is connected to an inlet of a B-Pump 116. The outlet of the B-Pump is connected to the outlet of the First Conductivity Cell and an inlet of a Second Mixing Chamber 117. The outlet of the Second Mixing Chamber is connected to the inlet of a Second Conductivity Cell 118 and the outlet of the Second Conductivity Cell constitutes the outlet of the Treatment Fluid Preparation Unit 110.

The outlet of the Treatment Fluid Preparation Unit 110 is connected to the inlet of a Flow Pump 120 and the outlet of the Flow Pump is connected to a Treatment Fluid Outlet 130. The path from the Inlet 101 to the Treatment Fluid Outlet 130 is referred to as the upstream portion of the Treatment Fluid Path. The temperature of the Treatment Fluid Path is normally measured by a Treatment Fluid Path Temperature Sensor 119 which in principle could be located anywhere in the Treatment Fluid Path downstream the Treatment Fluid Path Heater 104 (even in the downstream portion of the Treatment Fluid Path). In the embodiment shown in FIG. 1, the Treatment Fluid Path Temperature Sensor is located at the end of the upstream portion of the Treatment Fluid Path, in the vicinity of the Treatment Fluid Outlet 130, thereby providing a good measure of the temperature of the treatment fluid which is about to enter the dialyzer (when connected).

During dialysis treatment, the Treatment Fluid Outlet 130 would be connected to the treatment fluid inlet (not shown) of the dialyzer (not shown) by means of a Treatment Fluid Supply Tube 131 thereby providing treatment fluid to the treatment fluid side of the semi-permeable membrane of the dialyzer as mentioned above. After having passed the dialyzer, the treatment fluid exits the dialyzer at an outlet (not shown) and it is returned by means of a Treatment Fluid Return Tube 132 to a Treatment Fluid Return Inlet 133 which constitutes the start of the downstream portion of the Treatment Fluid Path of the Dialysis Monitor 100.

The Treatment Fluid Supply Tube 131 is provided with a First Connector 134 which, when connected to the Dialysis Monitor 100, engages with the Treatment Fluid Outlet 130. Similarly, the Treatment Fluid Return Tube 132 is provided with a Second Connector 139 which, when connected to the Dialysis Monitor 100, engages with the Treatment Fluid Return Inlet 133.

At the time the dialyzer is not connected to the Treatment Fluid Path (for example which may be the case at the time of start-up of the Treatment Fluid Preparation Unit, after the dialysis treatment, or during disinfection of the Treatment Fluid Path) the Treatment Fluid Supply Tube 131 and the Treatment Fluid Return Tube 132 may be connected by means of a Bypass Conduit 140 provided in the Dialysis Monitor. In detail, the Bypass Conduit 140 is provided with a Supply Tube Parking Connector 136 and a Return Tube Parking Connector 137 at each end of the Bypass conduit 140. The Treatment Fluid Supply Tube 131 is provided with a Third Connector 138 which, when connected to the Dialysis Monitor 100, engages with the Supply Tube Parking Connector 136. Similarly, the Treatment Fluid Return Tube 132 is provided with a Fourth Connector 135 which, when connected to the Dialysis Monitor 100, engages with the Return Tube Parking Connector 137.

The Treatment Fluid Return Inlet 133 is connected to the inlet of a Suction Pump 121 and the outlet thereof is connected to the inlet of the second side of the Heat Exchanger 103. The outlet of the second side of the Heat Exchanger is connected to an Exit 122. The Exit 122, which constitutes the end of the downstream portion of the Treatment Fluid Path of the Dialysis Monitor, is normally connected to a drain (not shown).

Other examples of the design of the Treatment Fluid Path, which may for example include additional sensors, actuators, tubes, chambers, etc., are well known in the art and may be combined with any one of the embodiments of the present invention.

The dialysis monitor further comprises a Tank 150 which is connected to the Treatment Fluid Path. The tank may be connected to the Treatment Fluid Path at a location upstream the connection point of the dialyzer. In the embodiment of FIG. 1, the tank is connected to the Treatment Fluid Path after the Heat Exchanger 103. A Tank Valve 151 is arranged between the Treatment Fluid Path and the Tank which, when open, allows fluid from the Treatment Fluid Path to enter or exit the Tank and, when closed, prevents fluid of the Tank to exit the Tank. The Tank further comprises an Expansion Exit 152 enabling air to enter and exit the tank as required to enable fluid to enter and exit the tank. In the particular embodiment of FIG. 1, the Tank is equipped with a Tank Heater 153, for enabling heating of the fluid of the tank, and a Tank Temperature Sensor 154, for enabling the temperature of the fluid of the Tank to be measured.

The Dialysis Monitor further comprises a Controller 160 and a User Interface 161. The Controller is operably connected to valves, heaters, pumps, temperature sensors, and other functional elements of the Dialysis Monitor, and is configured to read measured values and control the function of the functional elements. The Controller is further configured, by means of, analogue and/or digital circuits, and/or logic and/or micro-controllers, or similar, appropriately programmed by mean of software code, to carry out the functional steps of the operation of the Dialysis Monitors as disclosed in the various embodiments of the present invention. The Controller 160 is also connected to the User Interface 161, which may be a touch screen, in order to enable the displaying and entering of information to and from a user (not shown). It should be understood that certain activities, such as the starting, pausing and ending of dialysis treatment, the starting of disinfection of the Dialysis Monitor, etc., may be initiated by the user through the User Interface.

In certain embodiments, such as the embodiment illustrated in FIG. 1, a Second Inlet Valve 105 is provided between the location where the tank is connected to the Treatment Fluid Path (more precisely where the Tank Valve 151 connects to the Treatment Fluid Path) and the Treatment Fluid Path Heater 104. The Second Inlet Valve, when closed, enables the Dialysis Monitor 100 to direct all incoming fluid from the Inlet into the Tank (provided the Inlet Valve 102 and the Tank Valve 151 are open).

In operation, when dialysis treatment is performed by the Dialysis Monitor 100, the Controller 160 is programmed to set the Inlet Valve 102 and the Second Inlet Valve 105 in a fluidly open state whereas the Tank Valve 151 is set in a fluidly closed state. Water (normally purified water provided from a water supply system (not shown)) is thereby let in through the Inlet 101, the Inlet Valve 102, the first side of the Heat Exchanger 103, the Second Inlet Valve 105 and the Treatment Fluid Path Heater 104 and further into the Treatment Fluid Preparation Unit 110. In the Treatment Fluid Preparation Unit 110, A-concentrate from the A-Concentrate Container 111 is mixed into the Treatment Fluid Path by the Controller operating the A-Pump 112 and, after having been contained in the First Mixing Chamber 113, is let further through the First Conductivity Cell 114. The Controller is programmed to read the conductivity as measured by the First Conductivity Cell 114 and the measure is used by the Controller to calculate a control signal which it uses to control the A-Pump in order to arrive at a set mixture of A-concentrate and water. Similarly, B-Concentrate from the B-Concentrate Container 115 is mixed into the Treatment Fluid Path by the Controller operating the B-Pump 116 and, after having been contained in the Second Mixing Chamber 117, is let further through the Second Conductivity Cell 118. The Controller is programmed to read the conductivity as measured by the Second Conductivity Cell 114 and the measure is used by the Controller to calculate a control signal which it uses to control the B-Pump in order to arrive at a set mixture of B-concentrate in the treatment fluid, taking into account the A-concentrate already mixed with the water. The treatment fluid thereafter exits the Treatment Fluid Preparation Unit 110 and is moved forward in the Treatment Fluid Path by means of a Flow Pump 120 towards the Treatment Fluid Outlet 130.

The Controller 160 is programmed to read the temperature of the treatment fluid as measured by the Treatment Fluid Path Temperature Sensor 119 and to control the Treatment Fluid Path Heater 104 in order to arrive at a temperature during dialysis treatment which has been pre-set (e.g. at 37° C.) or which may have been a temperature set by a user through the User Interface 161 (and thereby made available to the Controller 160). In the latter case, the temperature of the treatment fluid during dialysis treatment is set at a temperature in the range of body temperature, for example in the range of 36° C. to 38° C., or in the range of 35° C. to 39° C., or in the range of 34° C. to 41° C.

As mentioned above, at the time dialysis treatment is being performed, the Treatment Fluid Outlet 130 would be connected to the treatment fluid inlet (not shown) of the dialyzer (not shown) by means of the Treatment Fluid Supply Tube 131 thereby providing treatment fluid to the treatment fluid side of the semi-permeable membrane of the dialyzer. After having passed the dialyzer, the treatment fluid exits the dialyzer at the outlet (not shown) and it is returned by means of the Treatment Fluid Return Tube 132 to the Treatment Fluid Return Inlet 133.

The now used treatment fluid is moved forward by means of the Suction Pump 121 and, after having passed the Suction Pump 121, it flows through the second side of the Heat Exchanger 103 before it exits the Dialysis Monitor 100 through the Exit 122. The fluid is thereafter often led to a drain (not shown) or a collecting bag or canister (not shown). The Heat Exchanger 103 allows the used treatment fluid, which has been heated to a temperature of approximately body temperature, to transfer heat over to the fresh water being received at the Inlet 101.

The functionality of the Tank 150 according to the first embodiment will now be discussed. The Controller 160 is programmed to enable fluid to be conveyed to/allowed to enter the Tank 150 by setting the Tank Valve 151 in a fluidly open state. The fluid is pushed into the Tank 150 due to the pressure of the fluid at the Inlet 101. The Controller 160 may set the Second Inlet Valve 105 in a fluidly closed state which will lead to that fluid will enter the Tank 150 quicker. As fluid enters the Tank 150, air present in the tank will be allowed to exit the Tank 150 through the Expansion Exit 152. The filling of the Tank 150 with the fluid may be continued until a set volume (e.g. measuring the flow rate) or level (e.g. measuring the fluid level in the Tank) of fluid has been reached or for a set duration of time. Without limitation to the present invention, the volume may be arrived at by measuring the flow rate of fluid into the Tank using a flow meter (not shown) or calculating the required time to fill the Tank based on a known (minimum) fluid inlet pressure or as measured by a pressure meter (not shown); the level may be measured by a level sensor (not shown); other methods are disclosed in embodiments and variants that follows. Thereafter the Controller 160 is programmed to set the Tank Valve 151 in a fluidly closed state. The fluid of the Tank will thereby be held in the Tank 150 as long as the Tank Valve 151 is in its closed state.

In a variation of the present invention, a separate pump (not shown), for example located in series with the Tank Valve 151, or even replacing the Tank Valve 151, can be used for pumping fluid into the Tank. In a further variation of the present invention, the Flow Pump 120 can be used to pump fluid into the Tank 150.

The Controller 160 is programmed to heat the fluid which is held in the Tank 150 by controlling the Tank Heater 153. As the fluid is held in the Tank 150, and is not able to mix with the fluid of the Treatment Fluid Path, the fluid in the Tank can be heated to a temperature which is higher than the temperature of the treatment fluid (as set for dialysis treatment, that is at about body temperature) without influencing the temperature of the treatment fluid. Consequently, the heating of the fluid in the Tank can take place at the same time as dialysis treatment is being performed by the Dialysis Monitor 100 even when the temperature is higher or much higher than the temperature of the dialysis treatment fluid as used during dialysis treatment. The higher or much higher temperature may for example be in the range of 40° C. to 99° C., 50° C. to 99° C., 60° C. to 99° C., 70° C. to 99° C., 80° C. to 99° C., 85° C. to 95° C., and/or 90° C. to 99° C.

The Controller 160 may read the temperature of the fluid in the Tank 150 as measured by the Tank Temperature Sensor 154 and may calculate a control signal used to control the Tank Heater 153 such that the fluid in the Tank is heated to a set temperature. The Controller 160 may perform this operation continuously, regularly or occasionally. The set temperature may be fixed in the Dialysis Monitor (e.g. 90° C.) or may be set by a user through the User Interface 161 and thereby be made available to the Controller 160. The set temperature may for example be in the range of 40° C. to 99° C., 50° C. to 99° C., 60° C. to 99° C., 70° C. to 99° C., 80° C. to 99° C., 85° C. to 95° C., and/or 90° C. to 99° C.

Thermal disinfection may be carried out at a time when dialysis treatment is not being performed. The dialyzer is then disconnected and the Third Connector 138 at the Treatment Fluid Supply Tube 131 is instead connected to the Supply Tube Parking Connector 136 and the Fourth Connector 135 at the Treatment Fluid Return Tube 132 is instead connected to the Return Tube Parking Connector 137. The upstream and downstream portions of the Treatment Fluid Path will thereby be connected together by means of the Bypass Conduit 140 and thermal disinfection of both these portions of the Treatment Fluid Path will be possible by letting hot fluid through the Treatment Fluid Path.

To achieve such thermal disinfection, the Dialysis Monitor 100 is configured to discharge the fluid held in the Tank 150 into the Treatment Fluid Path. Disinfection may be commenced by a command given by a user through the User Interface 161. At the time of thermal disinfection, the Controller 160 is programmed to set the Tank Valve 151 in a fluidly open state whereby hot fluid is exiting the Tank 150 and entering the Treatment Fluid Path. The Controller 160 also sets the Inlet Valve 102 in a fluidly closed state, the Second Inlet Valve 105 in a fluidly open state, and controls the Flow Pump 120 and the Suction Pump 121 in order to convey and move the hot fluid in the Treatment Fluid Path from the Tank 150 all the way through the Treatment Fluid Path to the Exit 122, that is through the Second Inlet Valve 105, the Treatment Fluid Path Heater 104, the Treatment Fluid Preparation Unit 110, the Flow Pump 120, the Treatment Fluid Supply Tube 131, the Bypass Conduit 140, the Treatment Fluid Return Tube 132, the Suction Pump 121, and the Heat Exchanger 103, as well as other components which may be present in the Treatment Fluid Path.

In a variation of the present invention, the discharged fluid may be further heated, for example by the Controller 160 being programmed to activate the Treatment Fluid Path Heater 104 during thermal disinfection. In yet a further variation, such further heating is only performed if the fluid discharged from the Tank has not reached a sufficiently high temperature to efficiently achieve thermal disinfection of the Treatment Fluid Path.

Fluid is thereafter allowed to enter the Tank 150 anew. This is achieved by the Controller 160 being programmed to enable fluid to be conveyed to/allowed to enter the Tank 150 by setting the Inlet Valve 102 and the Tank Valve 151 in fluidly open states as described above.

Thermal disinfection is thereby achieved in a much shorter time compared to known systems where water is heated to a sufficiently high temperature for thermal disinfection after the completion of a dialysis treatment. As an illustration, if it is assumed that the volume of the Treatment Fluid Path to be disinfected is 2.5 liter, the temperature of water entering the Treatment Fluid Path at the Inlet 101 has a temperature of 10° C., and the desired temperature of water used for thermal disinfection is 95° C. Under these conditions, the required energy to heat the water is 892 kJ (the specific heat capacity of water is 4.2 Joule/gram; the specific heat capacity of steel and plastic components in the Treatment Fluid Path is less than 1 Joule/gram and hence has been assumed to be negligible in comparison to the specific heat capacity of water; required energy=2500 g*4.2 J/g*(95° C.-10° C.)=892 kJ). If it is further assumed that the maximum available power from the mains (external power supply) is 1000 W, then the time to heat the required volume of water to the desired temperature for thermal disinfection takes 892 seconds or almost 15 minutes. If hot water from a tank is used instead of such heating after the dialysis treatment, then the time-between-treatments could be reduced with approximately 15 minutes which, in the context, is a significant period of time.

After the disinfection of the Treatment Fluid Path, dialysis treatment can be initiated anew as described above, possibly after the Treatment Fluid Path has been rinsed and the Treatment Fluid Preparation Unit has commenced its function to provide properly mixed treatment fluid.

In an alternative embodiment of the present invention, which may be combined with any other embodiment of the present invention, the Controller 160 is programmed to read the temperature of the fluid in the Tank 150 as measured by the Tank Temperature Sensor 153, and to compare the read temperature with a set temperature, the set temperature representing a temperature which is required in order to enable thermal disinfection of the Treatment Fluid Path, and provide an indication to the user through the User Interface 161 if the temperature of the Tank has reached and/or exceeds the set temperature and thereby indicating to the user that thermal disinfection can be performed. The set temperature may for example be set at 90° C. or in the range of for example 80° C. to 90° C. or 90° C. to 99° C.

In an alternative embodiment of the present invention, which may be combined with any other embodiment of the present invention, the Controller 160 is programmed to set the Inlet Valve 102 and the Tank Valve 151 in a fluidly open state, thereby filling the tank with fluid, at a time when hot fluid is being moved through the second side of the Heat Exchanger 103, that is at a time when the Controller 160 controls the Flow Pump 120 and the Suction Pump 121 to pump hot fluid present in the Treatment Fluid Path (e.g. at a final stage of thermal disinfection) towards the Exit 122. The hot fluid passing through the second side of the Heat Exchanger 103 will transfer energy to the fluid at the first side of the Heat Exchanger, that is fluid which has recently entered the Inlet 101, thereby heating the fluid received at the Inlet 101 before it is conveyed to the Tank 150. The heated fluid entering the Tank 150 does thereby have an elevated temperature leading to an energy efficient system where heat is returned from the hot water leaving the Dialysis Monitor 100 to incoming fluid which is intended to be heated (and to be held in the tank) prior to the next thermal disinfection event.

In an alternative embodiment of the present invention, which may be combined with any other embodiment of the present invention, the Controller 160 is programmed to control the Tank Heater 153 in such a way that the overall power consumed by the Dialysis Monitor does not exceed a maximum available power. For example, the Controller 160 may be programmed to limit the power supplied to the Tank Heater, thereby possibly reducing the heating speed of the fluid in the Tank, in order to secure that the overall consumed power is within the maximum value. A dialysis treatment is normally performed during a period of 4 hours which means that there would normally be sufficient time available to heat the fluid in the Tank, during the dialysis treatment, to a temperature sufficiently high in order to achieve thermal disinfection of the Treatment Fluid Path when the heated fluid is discharged from the Tank (after the dialysis treatment has been performed), even if the heating of the fluid in the Tank is performed slowly.

As an illustration, using the assumption above that the energy required to heat a required volume of 2.5 liter from 10° C. to 95° C. would be 892 kJ but now assuming the power used for the heating is 100 W, the time to heat the water would be 8920 seconds or 2 hours and 28 minutes. As a dialysis treatment normally lasts for approximately 4 hours, there will be ample of time to heat the water to be used for thermal disinfection using only 100 W while dialysis treatment is being performed.

Figure 2:
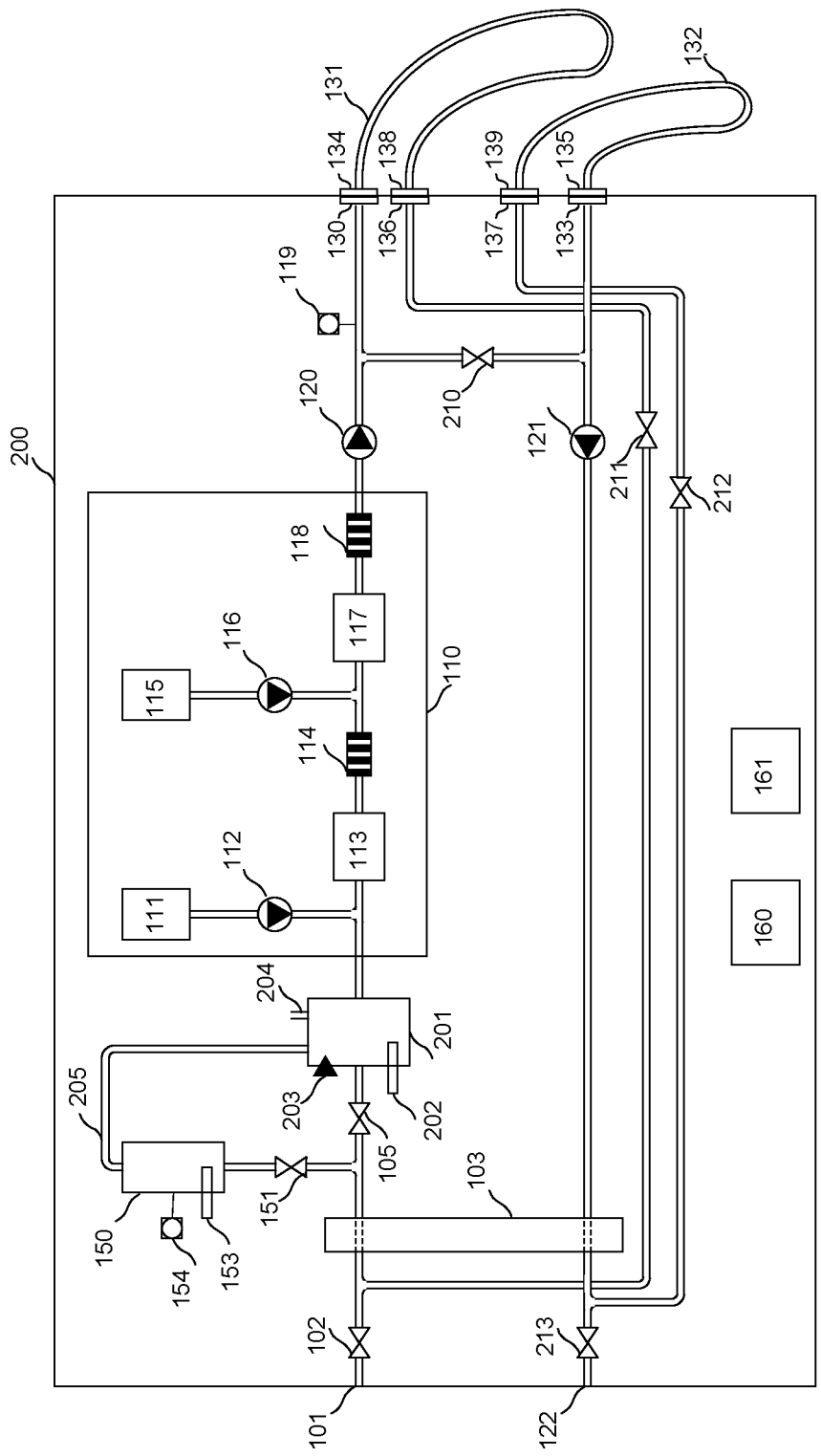
FIG. 2 shows a schematic diagram of a portion of a dialysis monitor according to an alternative embodiment of the present invention.

FIG. 2 shows a schematic diagram of a portion of a dialysis monitor according to an alternative embodiment of the present invention. Elements corresponding to elements present in the schematic diagram of FIG. 1 have been labelled with the same reference numbers. It should be understood, though, that the Controller 160 may be programmed differently in order to enable it to carry out the functionality of the embodiments disclosed in following.

The Dialysis Monitor 200 of the embodiment schematically shown in FIG. 2 comprises a Heating Vessel 201 equipped with a Heating Vessel Heater 202, which is configured to heat fluid present in the Heating Vessel 201. The Heating Vessel 201 further comprises a Level Sensor 203 and a Heating Vessel Expansion Exit 204. In this embodiment, the Expansion Exit 152 of the embodiments discussed in conjunction with FIG. 1 is now connected by an Expansion Tube 205 to the Heating Vessel 201. The inlet of the Heating Vessel 201 is connected to the downstream end of the Second Inlet Valve 105 and the outlet of the Heating Vessel 201 is connected to the inlet of the Treatment Fluid Preparation Unit 110. That is, the Heating Vessel 201 is replacing the Treatment Fluid Path Heater 104 of the embodiments disclosed in conjunction with FIG. 1.

In operation, when dialysis treatment is performed by the Dialysis Monitor 200, the Controller 160 is programmed to perform dialysis treatment in the same manner as discussed above in conjunction with the embodiments of FIG. 1 with the distinction that the Controller 160 is programmed to control the Heating Vessel Heater 202 in order to arrive at a temperature of the treatment fluid which has been pre-set (e.g. at 37° C.) or which may have been set by a user through the User Interface 161 (and thereby made available to the Controller 160). The use of a Heating Vessel 201 facilitates the maintaining of the temperature in the Treatment Fluid Path at the set temperature. The Controller 160 is also programmed to read the level of the fluid in the Heating Vessel 201 from the measurement made by the Level Sensor 203. The read level of the fluid in the Heating Vessel 201 enables the Controller to control the amount of fluid present in the Heating Vessel 201 by opening and closing the Inlet Valve 102 and the Second Inlet Valve 105 and controlling the Flow Pump 120 and the Suction Pump 121. Furthermore, any tendency of overpressure in the Tank 150 will be reduced due to the Expansion Tube 205, as the Expansion Tube 205 enables gas and fluid to escape the Tank 150 and instead enter the Heating Vessel 201. Additionally, overpressure in the Heating Vessel 201 is avoided due to the Heating Vessel Expansion Exit 204 which connects the Heating Vessel 201 to the atmosphere (at the upper part of the Heating Vessel 201).

Similarly to the embodiments discussed in conjunction with FIG. 1, the Controller 160 is programmed to enable fluid to be conveyed to/allowed to enter the Tank 150 by setting the Tank Valve 151 in a fluidly open state. The fluid is pushed into the Tank 150 due to the pressure of the fluid at the Inlet 101. The Controller 160 may set the Second Inlet Valve 105 in a fluidly closed state which will lead to that fluid will enter the Tank 150 quicker. As fluid enters the Tank 150, air present in the Tank 150 will be allowed to exit the Tank 150 through the Expansion Tube 205, continuing into the Heating Vessel 201 and further out through the Heating Vessel Expansion Exit 204. The filling of the Tank 150 with the fluid may be continued until the Controller 160 recognizes that a certain volume has been contained in the Tank or that it is full. In one embodiment, Controller 160 repeatedly reads the level of fluid in the Heating Vessel 201 as measured by the Level Sensor 203 when fluid is allowed to enter the Tank 150. As of the time when the level of fluid in the Tank 150 has reached the level when fluid in the Tank 150 will exit the Tank 150 through the Expansion Tube 205 and flow into the Heating Vessel 201, the fluid exiting the Tank 150 will add to the fluid present in the Heating Vessel 201. The added fluid will increase the level of the fluid in the Heating Vessel 201. The Controller 160, by repeatedly reading the level of fluid in the Heating Vessel 201 as measured by the Level Sensor 203, is programmed to stop the filling of fluid into the Tank 150 by setting the Tank Valve 151 in a fluidly closed state when the level of fluid in the Heating Vessel 201 exceeds a set value and/or the increase of fluid in the Heating Vessel 201 exceeds a set value. Alternatively, the Controller is programmed to read the level of fluid in the Heating Vessel 201 at or about the time when fluid is allowed to enter the Tank 150 (referred to as the starting level), repeatedly read the level of fluid in the Heating Vessel 201, compare the read level of fluid in the Heating Vessel 201 with the starting level, and stop the filling of fluid into the Tank 150 when the read level of fluid the Heating Vessel 201 reaches and/or exceeds the starting level with a set value. The filling of fluid into the Tank 150 is completed by the Controller being programmed to set the Tank Valve 151 in a fluidly closed state. The fluid of the Tank will thereby be held in the Tank 150 as long as the Tank Valve 151 is in its closed state.

FIG. 2 also shows an alternative Treatment Fluid Path which may be combined with or replacing the Treatment Fluid Path of other embodiment(s) of the present invention. As seen from FIG. 2, the Bypass Conduit 140 is replaced by a Bypass Valve 210 which on one end is connected to the Treatment Fluid Path at a location upstream the dialyzer (when connected), preferably at a location close to the Treatment Fluid Outlet 130, and at the other end is connected to the Treatment Fluid Path at a location downstream the dialyzer (when connected), preferably at a location close to the Treatment Fluid Return Inlet 133. An Exit Valve 213 is introduced between the outlet of the second side of the Heat Exchanger 103 and the Exit 122. Furthermore, the Supply Tube Parking Connector 136 is connected to one side of a First Return Valve 211 and the other end of the First Return Valve 211 is connected to the Treatment Fluid Path at a location downstream the Inlet Valve 102 but upstream the first side of the Heat Exchanger 103. The Return Tube Parking Connector 137 is connected to one side of a Second Return Valve 212 and the other end of the Second Return Valve 212 is connected to the Treatment Fluid Path at a location upstream the Exit Valve 213 but downstream the second side of the Heat Exchanger 103.

In operation, when dialysis treatment is performed by the Dialysis Monitor 201, the Controller 160 is programmed to perform dialysis treatment in the same manner as discussed above with the addition that the Controller 160 is programmed to set the First Return Valve 211, the Second Return Valve 212, and the Bypass Valve 210 in fluidly closed states.

At the time of disinfection, the disinfection may be carried out separately for the upstream portion of the Treatment Fluid Path and for the downstream portion of the Treatment Fluid Path. This is achieved by the Controller 160 being programmed to set the Inlet Valve 102, the Exit Valve 213 and the Bypass Valve 210 in fluidly close states, and to set the First Return Valve 211 and the Second Return Valve 212 in fluidly open states. A first circulation loop is thereby formed by the upstream portion of the Treatment Fluid Path (downstream the Inlet Valve 102 to the Treatment Fluid Outlet 130), the Treatment Fluid Supply Tube 131 and the tubing from the Supply Tube Parking Connector 136 to the Treatment Fluid Path at a location downstream the Inlet Valve 102 but upstream the first side of the Heat Exchanger 103. A second circulation loop is formed by the downstream portion of the Treatment Fluid Path (from the Treatment Fluid Return Inlet 133 to the Exit Valve 213), the tubing therefrom to the Return Tube Parking Connector 137, and the Treatment Fluid Return Tube 132. The fluid in the first circulation loop and the second circulation loop can be circulated by means of the Flow Pump 120 and the Suction Pump 121, respectively. The advantage of establishing two separate circulation loops is that fluid from the upstream portion of the Treatment Fluid Path, which may be contaminated by easy-to-remove waterborne bacteria and microorganisms from the treatment fluid, is not mixed with fluid from the downstream portion of the Treatment Fluid Path, which additionally may be contaminated by hard-to-remove blood borne virus, such as Hepatitis B.

Similarly to the embodiments discussed in conjunction with FIG. 1, the Dialysis Monitor 200 is configured to perform thermal disinfection of the Treatment Fluid Path by discharging the fluid held in the Tank 150 into the Treatment Fluid Path. In addition to establishing the first and second circulation loops, the Controller is programmed to set the Tank Valve 151 in a fluidly open state thereby enabling the hot water of in the Tank 150 to enter into the first circulation loop. The fluid in the second circulation loop may be heated by transfer of heat from the fluid in the first circulation loop to the fluid in the second circulation loop by means of the Heat Exchanger 103 and/or hot fluid may be allowed to enter the second circulation loop by (temporary) setting the Bypass Valve 210 in a fluidly open state. In the latter case, the Controller is programmed to set the Exit Valve 213 in a fluidly open state when the Bypass Valve is in a fluidly open state and fluid is allowed to enter the second circulation loop. The Controller is programmed to control the Flow Pump 120 and the Suction Pump 121 in order to circulate the hot fluid in the first and second circulation loops for a period of time, thereby thermally disinfect the Treatment Fluid Path.

Figure 3:
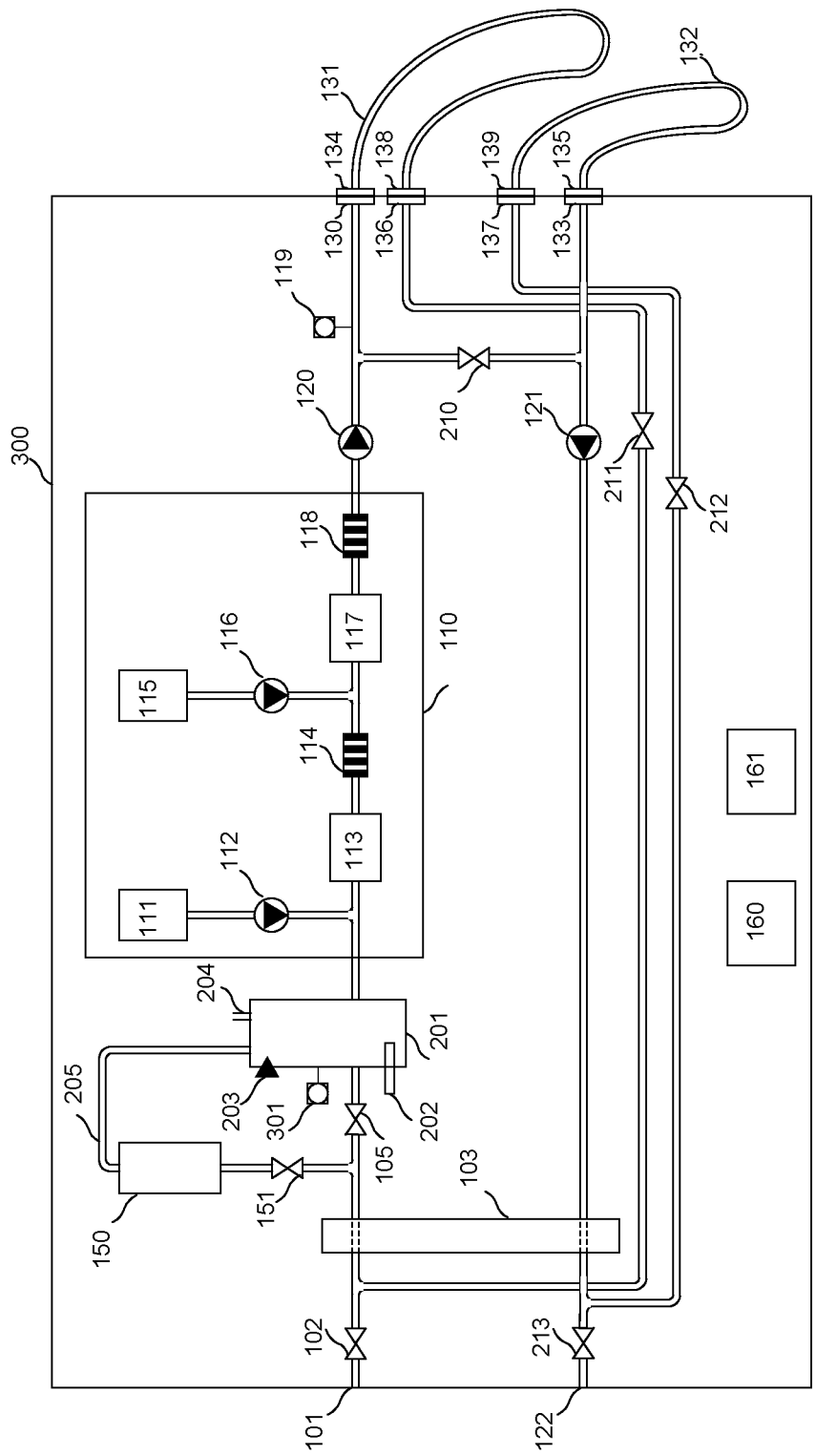
FIG. 3 shows a schematic diagram of a portion of a dialysis monitor according to a further alternative embodiment of the present invention.

FIG. 3 shows a schematic diagram of a portion of a Dialysis Monitor according to a further alternative embodiment of the present invention. Elements corresponding to elements present in the schematic diagrams of FIG. 1 and FIG. 2 have been labelled with the same reference numbers. It should be understood, though, that the Controller 160 may be programmed differently in order to enable it to carry out the functionality of the embodiments disclosed in following.

The Dialysis Monitor 300 of the embodiment schematically shown in FIG. 3 differs from the embodiment(s) schematically shown in FIG. 2 by not having a Tank Heater 153 and a Tank Temperature Sensor 154 but having a Heating Vessel Temperature Sensor 301 which is configured to measure the temperature of the fluid in the Heating Vessel 201.

The fluid to be used for thermal disinfection according to this embodiment is heated by the Heating Vessel Heater 202. The Controller 160 may be programmed to read the temperature of the fluid in the Heating Vessel 201 as measured by the Heating Vessel Temperature Sensor 301, and to compare the read temperature with a set temperature, the set temperature representing a temperature which is required in order to enable thermal disinfection of the Treatment Fluid Path, and provide an indication to the user through the User Interface 161 if the temperature of the Tank has reached and/or exceeds the set temperature and thereby indicating to the user that thermal disinfection can be performed. The set temperature may for example be set at 90° C. or in the range of for example 80° C. to 90° C. or 90° C. to 99° C.

Analogues to embodiments above, the Controller 160 is programmed to control the Flow Pump 120 and the Suction Pump 121 to thereby circulate the hot fluid in the first and second circulation loops for a period of time, thereby thermally disinfect the Treatment Fluid Path. At the final stage of the thermal disinfection, the Controller 160 is programmed to set the Inlet Valve 102, the Exit Valve 213, and the Bypass Valve 210 in fluidly open states and to continue the operation of the Flow Pump 120 and the Suction Pump 121, thereby pumping the hot fluid used during the thermal disinfection towards the Exit and further to the drain (not shown). At the same time, the Controller 160 is programmed to set the Tank Valve 151 in a fluidly open state and the Second Inlet Valve 105 in a fluidly closed state, thereby filling the tank with fluid at a time when hot fluid is being moved through the second side of the Heat Exchanger 103, that is, at a time when hot fluid present in the Treatment Fluid Path is being pumped towards the Exit 122 (that is, at the final stage of thermal disinfection). The hot fluid passing through the second side of the Heat Exchanger 103 will transfer energy to the fluid at the first side of the Heat Exchanger, that is, fluid which has recently entered the Inlet 101, thereby heating the fluid received at the Inlet 101 before it is conveyed to the Tank 150. The heated fluid entering the Tank 150 does thereby have an elevated temperature leading to an energy efficient system where heat is returned from the hot water leaving the Dialysis Monitor to incoming fluid which is intended to be heated (and to be held in the tank) prior to the next thermal disinfection event.

When the Tank 150 has been filled (which may be detected in a way as disclosed above) the Controller 160 is programmed to set the Tank Valve 151 in a fluidly closed state. Dialysis treatment may now be commenced whereby treatment fluid with a set temperature will be supplied to the dialyzer (as is explained above). At the same time, the Tank 150 will hold a fluid heated to a temperature which is higher than the temperature of the treatment fluid being provided during the dialysis treatment. The higher temperature of the fluid in the Tank 150 will not influence the temperature of the treatment fluid in the Treatment Fluid Path as the fluid in the Tank is now separated from the Treatment Fluid Path by means of the fluidly closed Tank Valve 151.

After the dialysis treatment, when thermal disinfection is to be initiated anew, the Dialysis Monitor 300 is configured to perform thermal disinfection of the Treatment Fluid Path by discharging the fluid held in the Tank 150 into the Treatment Fluid Path. If necessary, the discharged fluid may be further heated by the Controller 160 being programmed to activate the Heating Vessel Heater 202 in order to reach an even higher temperature of the fluid before and/or while being circulated in the first and second circulation loops.

In the same manner as described above, at the final stage of the thermal disinfection, the Controller 160 is programmed to set the Inlet Valve 102, the Exit Valve 213, and the Bypass Valve 210 in fluidly open states and to continue the operation of the Flow Pump 120 and the Suction Pump 121, thereby pumping the hot fluid used during the thermal disinfection towards the Exit and further to the drain (not shown). At the same time, the Controller 160 is programmed to set the Tank Valve 151 in a fluidly open state, thereby filling the tank with fluid at a time when hot fluid is being moved through the second side of the Heat Exchanger 103, that is at a time when hot fluid present in the Treatment Fluid Path is being pumped towards the Exit 122 (that is at the final stage of thermal disinfection). The hot fluid passing through the second side of the Heat Exchanger 103 will transfer energy to the fluid at the first side of the Heat Exchanger, that is fluid which has recently entered the Inlet 101, thereby heating the fluid received at the Inlet 101 before it is conveyed to the Tank 150. The heated fluid entering the Tank 150 does thereby have an elevated temperature leading to an energy efficient system where heat is returned from the hot water leaving the Dialysis Monitor 300 to incoming fluid which is intended to be heated (and will be held in the tank) prior to the next thermal disinfection event.

When the Tank 150 has been filled (which may be detected in a way as disclosed above) the Controller 160 is programmed to set the Tank Valve 151 in a fluidly closed state. Dialysis treatment may now be commenced anew whereby treatment fluid with a set temperature will be supplied to the dialyzer (as is explained above). At the same time, the Tank 150 will hold a fluid heated to a temperature which is higher than the temperature of the treatment fluid being provided during the dialysis treatment.

In an alternative embodiment where the Dialysis Monitor 300 is occasionally receiving hot fluid (for example at a temperature in the range of 80° C. to 90° C.) at the Inlet 101, to be used for thermal disinfection, from a central water supply system (not shown), the Controller may be programmed to convey at least some of the received hot water into the Tank 150 by setting the Tank Valve 151 in a fluidly open state (possibly after having emptied the Tank 150 by setting the Inlet Valve in a fluidly closed state and setting the Tank Valve 151 in a fluidly open state). Once the Tank has been filled (which may be detected in a way as disclosed above) the Controller 160 is programmed to set the Tank Valve 151 in a fluidly closed state. At a time when the Dialysis Monitor receives fluid intended to be used for dialysis treatment (that is, not heated purified water for example in the temperature range of 10° C.–20° C.), dialysis treatment may be commenced anew. Treatment fluid with a set temperature will be supplied to the dialyzer (as is explained above). At the same time, the Tank 150 will hold a fluid heated to a temperature which is higher than the set temperature of the treatment fluid being provided during the dialysis treatment. The higher temperature of the fluid in the Tank 150 will not influence the temperature of the treatment fluid in the Treatment Fluid Path as the fluid in the Tank is now separated from the Treatment Fluid Path by means of the fluidly closed Tank Valve 151.

After the dialysis treatment, for example in between treatments of two patients, when thermal disinfection is to be initiated anew and when hot fluid is normally not being received from the water supply system, the Dialysis Monitor 300 is configured to perform thermal disinfection of the Treatment Fluid Path by discharging the fluid held in the Tank 150 into the Treatment Fluid Path. If necessary, the discharged fluid may be further heated by the Controller 160 being programmed to activate the Heating Vessel Heater 202 in order to reach an even higher temperature of the fluid before and/or while being circulated in the first and second circulation loops.

In the same manner as described above, at the final stage of the thermal disinfection, the Controller 160 is programmed to set the Inlet Valve 102, the Exit Valve 213, and the Bypass Valve 210 in fluidly open states and to continue the operation of the Flow Pump 120 and the Suction Pump 121, thereby pumping the hot fluid used during the thermal disinfection towards the Exit and further to the drain (not shown). At the same time, the Controller 160 is programmed to set the Tank Valve 151 in a fluidly open state, thereby filling the tank with fluid at a time when hot fluid is being moved through the second side of the Heat Exchanger 103, that is at a time when hot fluid present in the Treatment Fluid Path is being pumped towards the Exit 122 (that is at the final stage of thermal disinfection). The hot fluid passing through the second side of the Heat Exchanger 103 will transfer energy to the fluid at the first side of the Heat Exchanger, that is fluid which has recently entered the Inlet 101, thereby heating the fluid received at the Inlet 101 before it is conveyed to the Tank 150. The heated fluid entering the Tank 150 does thereby have an elevated temperature leading to an energy efficient system where heat is returned from the hot water leaving the Dialysis Monitor to incoming fluid which is intended to be heated (and will be held in the tank) prior to the next thermal disinfection event.

When the Tank 150 has been filled (which may be detected in a way as disclosed above) the Controller 160 is programmed to set the Tank Valve 151 in a fluidly closed state. Dialysis treatment may now be commenced anew whereby treatment fluid with a set temperature will be supplied to the dialyzer (as is explained above). At the same time, the Tank 150 will hold a fluid heated to a temperature which is higher than the temperature of the treatment fluid being provided during the dialysis treatment.

In variations to the embodiments discussed above, the Dialysis Monitor 100, 200, 300, may be configured to convey fluid which has been used for disinfection and/or cleaning to the Tank. This is especially attractive when the dialysis Monitor is configured to enable a circulation loop to be formed within at least a portion of the treatment fluid path upstream the dialyzer (as discussed in conjunction with FIG. 2 and FIG. 3) as the fluid which has been used to disinfect and/or clean the fluid path upstream the dialyzer is not as contaminated as the corresponding fluid downstream the dialyzer and this fluid can thereby be re-used at one or several later disinfection and/or cleaning events. The fluid which has been used for disinfection and/or cleaning may for example be heated water and/or a (heated or non-heated) fluid comprising citric acid. The fluid which has been used for disinfection and/or cleaning at a first disinfection and/or cleaning event, and which subsequently is conveyed to and stored in the Tank, can be retained in the Tank while the Dialysis Monitor performs dialysis treatment on a patient, and thereafter be re-used for disinfection and/or cleaning at a subsequent disinfection and/or cleaning event when the Dialysis Monitor no longer performs dialysis treatment on a patient.

In a particular embodiment, disinfection of the upstream portion of the Treatment Fluid Path, that is, first circulation loop, is performed as discussed above in relation to FIG. 2 and FIG. 3. At the time disinfection of this portion is completed, the Controller 160 is programmed to open the Tank Valve 151 and close the Second Inlet Valve 105 (while maintaining the Inlet Valve 102 closed). The fluid in the first circulation loop is thereby made to flow into the Tank 150 by the Controller being programmed to operate the Flow Pump 120. The Controller is also programmed to thereafter close the Tank Valve 151 in order to retain the used disinfection fluid for the next disinfection event. The fluid in the second circulation loop is normally allowed to exit the Dialysis Monitor through the Exit 122 which is achieved by the Controller being programmed to open the Exit Valve 213 and operating the Suction Pump 121. The Treatment Fluid Path may thereafter be rinsed before the Dialysis Monitor is starting up the preparation of dialysis fluid and commencing dialysis treatment on a patient anew. After the dialysis treatment, disinfection of the Treatment Fluid Path is carried out again using the (used) disinfection fluid as previously stored in the Tank 150. This is achieved by the Controller being programmed to establish the first circulation loop again (as discussed above) and let disinfection fluid stored in the Tank into the Treatment Fluid Path by opening the Tank Valve 151 and circulate the disinfection fluid by operating the Flow Pump 120.

Figure 4:
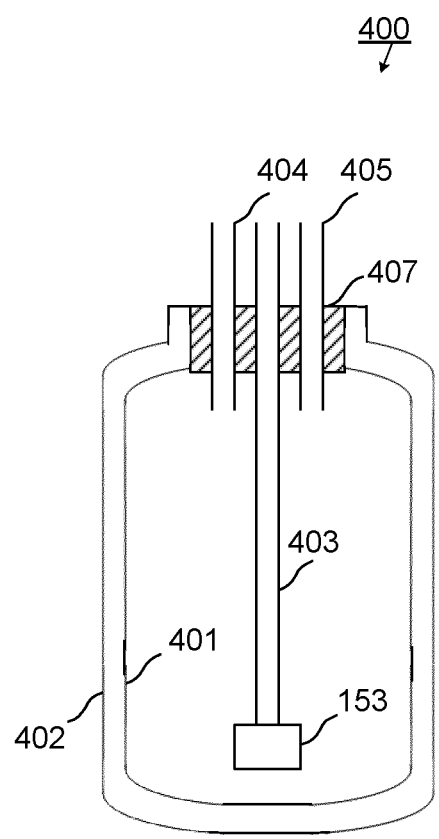
FIG. 4 depicts a cross-sectional view of a section of the tank arrangement according to an embodiment of the present invention.

When the Tank 150 holds fluid of a high temperature, there may be energy loss to the environment and thus the temperature of the fluid in the Tank may become lower with time. It is therefore advantageous to insulate the Tank 150. FIG. 4 depicts a cross-sectional view of a section of the Tank Arrangement 400 according to an embodiment of the present invention. According to this embodiment, which may be combined with any other embodiment of the present invention, the Tank 150 comprises an Inner Tank Wall 401 and an Outer Tank Wall 402. The space 406 between the Inner Tank Wall 401 and the Outer Tank Wall 402 may be filled with an insulating material, alternatively be void of matter (that is "contain" a vacuum thereby forming a structure equivalent to a thermos), in order to reduce the loss of heat from the fluid held in the Tank 150. In other variations of the present invention, other insulation methods may be possible, for example enclosing the complete Tank in an external insulator. FIG. 4 also shows an example where the Tank Heater 153 is located within the Tank 150. In this case, the Tank Heater 153 is connected by means of a Tank Heater Connector 403. FIG. 4 also shows a First Tank Pipe 404 (which is connected to the Tank Valve 151 in FIG. 1, FIG. 2 and FIG. 3 (not shown in FIG. 4)) for enabling fluid to enter and exit the Tank and a Second Tank Pipe 405 (which constitutes or forms part of the Expansion Exit 152 or is connected to the Expansion Tube 205 in the embodiments as shown in FIG. 1, FIG. 2. or FIG. 3 (not shown in FIG. 4)). According to the embodiment shown in FIG. 4, the First Tank Pipe 404, the Second Tank Pipe 405, and the Tank Heater Connector 403 are entering/exiting the Tank 150 through a single opening at the top of the Tank and the remaining opening from the Tank 150 is sealed off by a Seal 407 (shown by hashed line areas in FIG. 4).

In an alternative embodiment, which may be combined with any other embodiment of the present invention, the Tank 150 may comprise one or several tank walls and may be provided with one or several thermally insulating layer(s) which may substantially encompasses the Tank 150.

In an alternative embodiment, which may be combined with other embodiment(s) of the present invention, the fluid used for thermal disinfection may comprise chemical disinfection agents (for example, citric acid, lactic acid, malic acid or sodium carbonate, or combinations thereof).

In an alternative embodiment of the present invention, which may be combined with any other embodiment of the present invention, the Tank 150 is connected to the Treatment Fluid Path at a location upstream the first side of the Heat Exchanger 103.

In an alternative embodiment of the present invention, which may be combined with any other embodiment of the present invention, the Tank 150 is provided with a level sensor (not shown) which is configured to, or additionally configured to, sense that the Tank 150 has been emptied, or substantially emptied, from fluid. The Controller 160 may then be programmed to read the measure from the level sensor and, when thermal disinfection has been initiated by the discharging of fluid from the Tank, to control the Tank Valve 151 in order to set it in a fluidly closed state when it has recognized that the tank has been emptied.

In an alternative embodiment of the present invention, which may be combined with any other embodiment of the present invention, the Treatment Fluid Path Heater 104 may be located at a location upstream the location where the Tank 150 is connected to the Treatment Fluid Path. Similarly, the Heating Vessel 201 and the Heating Vessel Heater 202 may be located at a location upstream to the location where the Tank 150 is connected to the Treatment Fluid Path.

In an alternative embodiment of the present invention the fluid which is held by the Tank 150 may, at the time of thermal disinfection, be discharged into a first side of a second Heat Exchanger (not shown), the second side thereof forming part of the Treatment Fluid Path (instead of the fluid of the Tank 150 being discharged directly into the Treatment Fluid Path).

In an alternative embodiment of the present invention, the Tank Heater 151 may be located exterior to the Tank 150 as long as it still is able to heat fluid in the Tank 150 (including designs where fluid is extracted from the Tank 150, followed by heating of the extracted fluid, and thereafter returning the extracted heated fluid to the Tank 150).

The various embodiments discussed above may be combined in any manner in order to form alternative embodiments of the present invention.

To facilitate the understanding of the present invention, only elements required for the understanding of the present invention have been disclosed with the given embodiments. It should be understood that Dialysis Monitors of the present invention may comprise additional elements as known in the art without departing from the present invention.

Components, such as valves, clamps, and pumps, which may be used to control the flow of fluid in a conduit, are generally referred to as actuators.

An advantage, at least in respect of some embodiments of the present invention, is that thermal disinfection of the Dialysis Monitor can be achieved in a short period of time, thereby making the time-between-treatments shorter. This is achieved by the arrangement that the tank holds the fluid having a higher temperature at least for a period of time while the treatment fluid path is supplying treatment fluid at the first temperature during a dialysis treatment. There is thereby no or less need to perform time-consuming heating of the fluid to be used for thermal disinfection after dialysis treatment and before thermal disinfection can take place— the fluid in the tank is already at an elevated temperature when being discharged from the tank.

As an illustration of the time-consuming heating of fluid to be used for thermal disinfection, it may be assumed that the volume of the Treatment Fluid Path to be disinfected is 2.5 liter, the temperature of water entering the Treatment Fluid Path at the Inlet has a temperature of 10° C., and the desired temperature of water used for thermal disinfection is 95° C. Under these conditions, the required energy to heat the water is 892 kJ (the specific heat capacity of water is 4.2 Joule/gram; the specific heat capacity of steel and plastic components in the Treatment Fluid Path is less than 1 Joule/gram and hence has been assumed to be negligible in comparison to the specific heat capacity of water; required energy=2500 g*4.2 J/g*(95° C.−10° C.)=892 kJ). If it is further assumed that the maximum available power from the mains (external power supply) is 1000 W, then the time to heat the required volume of water to the desired temperature for thermal disinfection takes 892 seconds or almost 15 minutes. If no heating is required after the dialysis treatment, then the time-between-treatments could be reduced with approximately 15 minutes which, in the context, is a significant period of time.

Consequently, there is an advantage of a more efficient use of the Dialysis Monitors (e.g. measured in percentage of time available for dialysis treatment of patients at for example clinics and hospitals). The working hours of the operating staff (nurses and technicians, as the case may be, who operate the Dialysis Monitors) can be shortened which in turn has positive economic effects for the clinics/hospitals and also positive work environmental effects for the operating staff. Patients also benefit as the Dialysis Monitors are used more efficiently.

Another advantage, at least in respect of some embodiments of the present invention, is that since the fluid in the tank can be heated slowly the risk of overloading the power supply which is available to the Dialysis Monitor can be reduced/avoided (the maximum power supply available to the Dialysis monitor is limited by dimensions on power supply cables and related fuses).

As an illustration, using the assumption above that the energy required to heat a required volume of 2.5 liter from 10° C. to 95° C. would be 892 kJ but now assuming the power used for the heating is 100 W, the time to heat the water would be 8920 seconds or 2 hours and 28 minutes. As a dialysis treatment normally lasts for approximately 4 hours, there will be ample of time to heat the water to be used for thermal disinfection using only 100 W while dialysis treatment is being performed.

In an alternative embodiment of the present invention, which may be combined with any other embodiment of the present invention, hot fluid held in the Tank 150 is used to establish the treatment fluid at a set temperature. The set temperature may be set for example at 37° C. or at a temperature in the range of 34° C. to 41° C. The fluid held in the Tank is referred to as hot fluid when the fluid is warmer than the set temperature of the treatment fluid used by the Dialysis Monitor during dialysis treatment on a patient. That is, hot fluid may, for example be fluid with a temperature in the range of 80° C. to 90° C., or fluid with a temperature of at least 60° C. or at least 80° C.

In operation, and with reference to any one of the schematic diagrams of a portion of Dialysis Monitors 100, 200, 300 as shown in FIG. 1, FIG. 2 and FIG. 3, the hot fluid held in the Tank 150 is let out into the Treatment Fluid Path by the Controller 160 being programmed to fluidly open the Tank Valve 151. The hot water entering the treatment fluid path from the Tank will mix with fluid received at the Inlet 101. The fluid received at the Inlet 101 has a temperature which normally is in the range of 10° C. to 20° C. and which thereby is lower than the set temperature of the treatment fluid used by the Dialysis Monitor during dialysis treatment on a patient. The so mixed fluid will consequently have a temperature which is warmer than the temperature of the fluid entering through the Inlet but which is colder than the temperature of the fluid held in the Tank. By operating the Tank Valve, for example by fluidly opening and closing the Tank Valve during certain time intervals, respectively, the temperature of the so mixed fluid can be controlled. The Controller may read the temperature of the fluid in the Treatment Fluid Path, for example as measured by the Treatment Fluid Path Temperature Sensor 119, and control the fluidly open and closed time intervals of the Tank Valve based on the divergence from a reference value which in this case would be the set temperature of the treatment fluid to be used during dialysis treatment. The Controller may make use of a control algorithm such as a PID algorithm when controlling the Tank Valve in order to arrive at a temperature of the treatment fluid which substantially corresponds to the reference value (e.g. 37° C.).

In a particular example, the Controller 160 is programmed to let hot fluid held in the Tank 150 out into the Treatment Fluid Path when the Dialysis Monitor is starting up the preparation of treatment fluid and the Dialysis Monitor is not performing dialysis treatment on a patient. In this case, the temperature of the treatment fluid can quickly be increased to the set temperature. This would normally not be possible to achieve by means of the heater since the externally provided electrical power always is limited (due to installation, cable-dimensions, and maximum permitted current allowed by installed fuses) and the heater thereby cannot heat the treatment fluid when starting up the preparation of treatment fluid with the same speed.

In another particular example, the Controller 160 is programmed to let hot water held in the Tank 150 out into the Treatment Fluid Path when there is an interruption of externally provided electrical power to the Dialysis Monitor 100, 200, 300. A Dialysis Monitor normally receives externally provided electrical power from the mains. The received externally provided electrical power is used to power the functional elements of the Dialysis Monitors (such as the Controller 160, User Interface 161, actuators, pumps, etc.). Furthermore, a Dialysis Monitor may comprise a back-up battery (not shown in FIG. 1, FIG. 2, and FIG. 3)

which provides power should the externally provided electrical power be interrupted. In such situations, the Dialysis Monitor may use the power from the back-up battery to power the Controller 160 and other vital functional elements in order to stop the treatment in a controlled manner and to allow blood present in the extracorporeal blood circuit to be circulated or returned to the patient. The back-up battery does normally not have the capacity required to power the Dialysis Monitor for continued dialysis treatment, at least not for any extensive time, as such back-up battery then would have become bulky and expensive.

The most power consuming functional element of the Dialysis Monitor 100, 200, 300 during dialysis treatment is the Treatment Fluid Path Heater 104 or the Heating Vessel Heater 202 which, from a point of time during the start-up of the preparation of treatment fluid (that is, before dialysis treatment is being performed on a patient) and throughout the dialysis treatment, heats fluid provided to the Dialysis Monitor at the Inlet 101 to the set temperature in order to prepare treatment fluid of the set temperature for use by the Dialysis Monitor during dialysis treatment.

According to this alternative embodiment of the present invention, the Dialysis Monitor comprises a Power Interruption Detection Circuit (not shown in FIG. 1, FIG. 2, or FIG. 3)) which enables the Controller 160 to detect whether there is an interruption of the externally provided electrical power. This circuit may be designed in many different ways. One way is to make use of an AC/DC converter which is on its AC side coupled to the mains (externally provided electrical power) for example by means of an insulating transformer. The DC side of the AC/DC converter is connected to a comparator which provides defined (binary) signals at its output depending on whether the externally provided electrical power is interrupted or not. The output of the comparator is connected to the Controller 160 which thereby is able to detect whether there is an interruption of the externally provided electrical power. The circuit may receive its power from the back-up battery or simply enter a "low" binary signal (=OV) when the externally provided electrical power is interrupted. When the Controller detects an interruption of the externally provided electrical power during dialysis treatment, the Dialysis Monitor is configured to convey hot fluid from the Tank 150 in order to provide treatment fluid at substantially the set temperature. This may be achieved by conveying hot fluid from the Tank into the Treatment Fluid Path as discussed above. In other respects, the Controller controls the Dialysis Monitor to continue the treatment as if no interruption had occurred. At the time of interruption of externally provided electrical power, the Dialysis Monitor may be configured not to provide, or only provide limited amount of, electrical power from the back-up battery to the Heating Vessel Heater 202 in order to use the energy available in the back-up battery for, or substantially for, other functional elements than the Heating Vessel Heater 202. The time during which treatment may be continued without externally provided electrical power can thereby be extended. Consequently, the Heating Vessel Heater 202 may not be connected to the back-up battery at all or it may be limitedly connected to the back-up battery by means of one or several switch(es) (e.g. transistor(s) or thyristor(s)) (not shown) which in turn may be connected to and under control of the Controller 160. The Controller 160 is thereby able to control the amount of power (if any) provided from the back-up battery to the Heating Vessel Heater 202.

Figure 5:
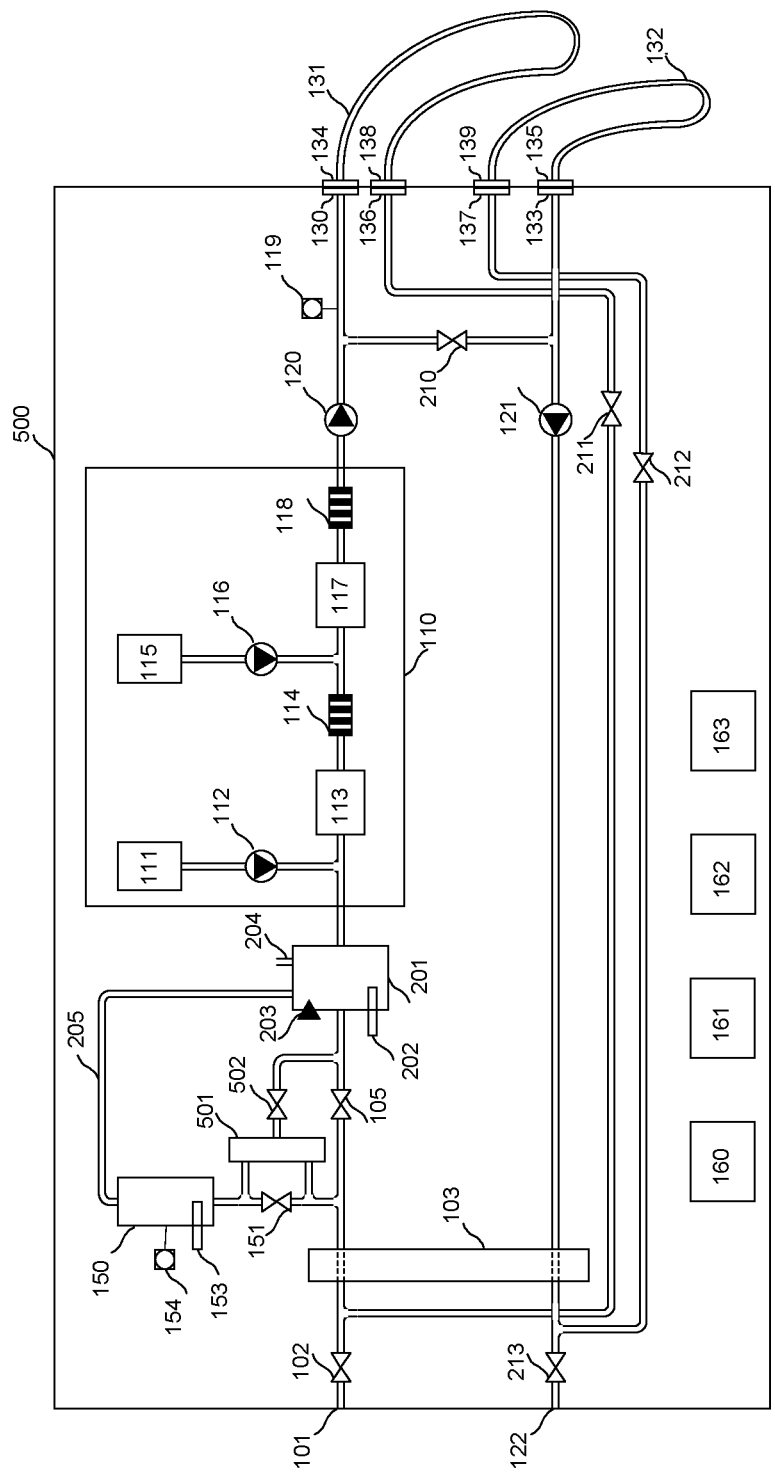
FIG. 5 shows a schematic diagram of a portion of a dialysis monitor according to yet a further alternative embodiment of the present invention.

FIG. 5 shows a schematic diagram of a portion of a Dialysis Monitor according to yet a further alternative embodiment of the present invention which may be combined with previous embodiments. Elements corresponding to elements present in the schematic diagrams of FIG. 1, FIG. 2, and FIG. 3 have been labelled with the same reference numbers in FIG. 5. It should be understood, though, that the Controller 160 may be programmed differently in order to enable it to carry out the functionality of the embodiments disclosed in following. FIG. 5 also shows the Back-up Battery 162 and the Power Interruption Detection Circuit 163 which have been discussed above (and any one of these two illustrations could be added to any one of the embodiments discussed in conjunction with FIG. 1, FIG. 2, or FIG. 3 to the extent a Back-up Battery 162 and/or a Power Interruption Detection Circuit 163 is/are present).

The Dialysis Monitor 500 of the embodiment schematically shown in FIG. 5 differs from the embodiment(s) schematically shown in FIG. 1, FIG. 2, and FIG. 3 by the introduction of a Fluid Mixer 501. A first inlet of the Fluid Mixer 501 is connected to the outlet on the first side of the Heat Exchanger 103, a second inlet of the Fluid Mixer 501 is connected to the Tank 150, and the outlet of the Fluid Mixer 501 is connected to a first side of a Mixer Valve 502, and the second side of the Mixer Valve 502 is connected to the downstream side of the Second Inlet Valve 105. The Tank Valve 151 is thereby located between the first and second inlet of the Fluid mixer 501.

In operation, and with reference to embodiments of the present invention discussed above where hot fluid held in the Tank 150 is used to establish the treatment fluid at a set temperature by letting hot water enter the treatment fluid path from the Tank and thereby mix with fluid received at the Inlet 101, the mixing of the embodiment shown in FIG. 5 is performed by the Fluid Mixer 501. Fluids entering at its inlets are mixed with a mixing ratio which either is fixed or adjustable. Similar to embodiments discussed above, fluid is allowed to enter the Tank by fluidly opening the Tank Valve 151 and, additionally, fluidly closing the Mixer Valve 502. At the time fluid should be allowed to enter the treatment fluid path from the Tank, the Tank Valve 151 is fluidly closed and the Mixer Valve 502 is fluidly opened.

In a variation of the present invention, the Fluid Mixer 501 is a Thermostatic Mixer. The Thermostatic Mixer adjusts the mixing ratio between the fluids entering at its inlets such that a target temperature is achieved for the so mixed fluid. The target temperature may be fixed (for example 37° C.) or adjustable. The advantage of using a Thermostatic Mixer is that the temperature of the mixed fluid, for example at the time of an interruption of externally provided electrical power as discussed above, is automatically controlled by the Thermostatic Mixer.

In a further variation of the present invention, the mixing ratio of the Fluid Mixer 501, or the target temperature if the Fluid Mixer is a Thermostatic Mixer, can be controlled by the Controller 160. This is achieved by a Mixer Actuating Unit (also referred to as an Adjustment Arrangement) which is configured to receive a signal from the Controller and to adjust the mixing ratio, or the target temperature if the Fluid Mixer is a Thermostatic Mixer, of the Fluid Mixer in response to the received signal. The Controller may then read the temperature of the fluid in the treatment fluid path, for example as measured by the Treatment Fluid Path Temperature Sensor 119, and control the mixing ratio, or the target temperature if the Fluid Mixer is a Thermostatic Mixer, of the Fluid Mixer by means of the Mixer Actuating Unit and based on the divergence from a reference value, which in this case would be the set temperature of the treatment fluid to be used during dialysis treatment. The Controller may make use of a control algorithm such as a PID algorithm when controlling the Mixer Actuating Unit in order to arrive at a temperature of the treatment fluid which substantially corresponds to the reference value (e.g. 37° C.).

Figure 6:
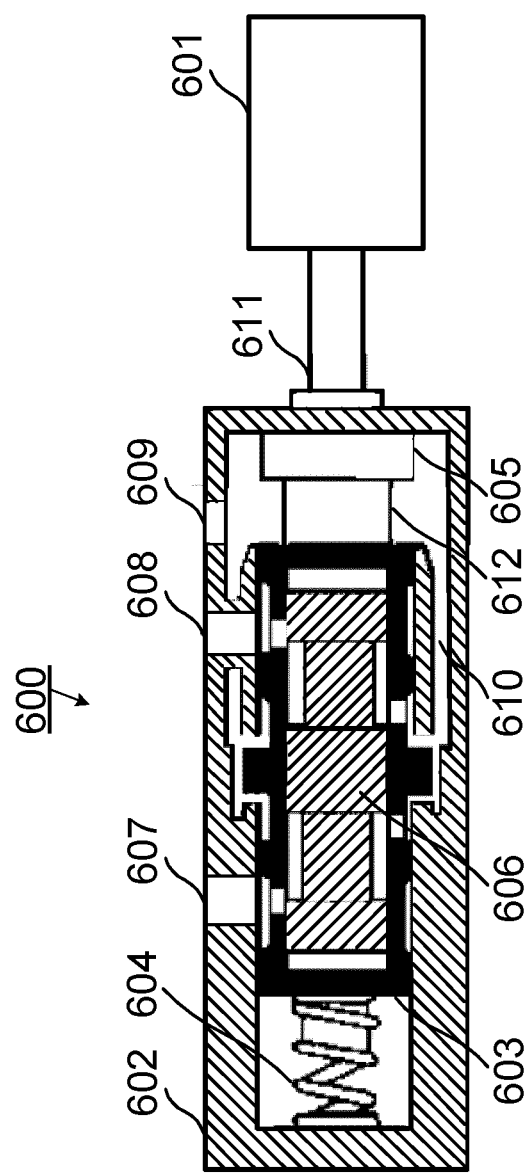
FIG. 6 shows a cross-sectional view of a thermostatic mixer and a mixer actuating unit.

A cross-sectional view of a Thermostatic Mixer 600 and a Mixer Actuating Unit 601 are shown in FIG. 6. The Thermostatic Mixer comprises a Housing 602 within which a Slide Valve 603 is mounted with means of a Spring 604 on one end and a Thermal Expansion Element 605, connected to the Slide Valve by means of a Connecting Member 612, on the other end. A Pressure Balancing Piston 606 is mounted within the Slide Valve. The Housing is provided with a Hot Fluid Inlet 607 and a Cold Fluid Inlet 608, configured to receive hot fluid and cold fluid, respectively, and a Mixer Outlet 609 through which mixed fluid is let out from the Thermostatic Mixer after having passed a Mixer Outlet Chamber 610. The Slide Valve is spring-loaded by means of the Spring and the force of the Spring is countered by the Thermal Expansion Element thereby setting the Slide Valve in a defined position at rest. An Axle 611 is configured to influence the defined position of the Slide Valve, either in direction of the Spring or in the direction of the Thermal Expansion Element. The Axle is, in turn, controlled by the Mixer Actuating Unit. The Axle may move axially in relation to the Housing by means of a threading when rotated. The Mixer Actuating Unit may then comprise a stepping motor which, when rotating, influences the position of the Axle.

In operation, the temperature is controlled in the Thermostatic Mixer 600 by a co-operation between pressure balancing and thermostatic controlling. The Pressure Balancing Piston 606 continuously adjusts its position such that the cold fluid and the hot fluid entering into the Pressure Balancing Piston have the same pressure. Since the Thermal Expansion Element 605 is located between the Axle 611 and the Slide Valve 603, and the length of the Thermal Expansion Element will vary depending on the temperature of the mixed fluid as appear in the Mixer Outlet Chamber 610, variations in the temperature of the cold and hot fluid at the Cold Fluid Inlet 608 and Hot Fluid Inlet 607 will be compensated and a very uniform temperature of the mixed fluid at the Mixer Outlet 609 will be achieved.

With reference to the embodiments discussed above, it should be understood that the Tank Valve 151 may be a valve which can only be in a fluidly opened or closed state or it may be any kind of actuator which can control the flow of fluid, including a valve which enables the degree of fluidly openness/closeness to be controlled in more detail (for example, a pump). Furthermore, several of the valves discussed may be combined in multi-way valves (for example, a three-way valve).

In case of embodiments of the present invention discussed above where hot fluid held in the Tank 150 is used to establish the treatment fluid at a set temperature by letting hot water enter the treatment fluid path from the Tank and thereby mix with fluid received at the Inlet 101 are combined with embodiments where disinfection and/or cleaning agents are stored in the Tank, a separate Tank (not shown) may be used, thereby separating purified water (to be used in the preparation of treatment fluid) held in a first Tank (not shown) and disinfection and/or cleaning fluid (possibly containing chemical agents) held in a second Tank (not shown). Hence, disinfection and/or cleaning agents are prevented from entering the treatment fluid to be used for dialysis treatment.

An advantage, at least in respect of some embodiments of the present invention, is that impact of interruption in externally provided electrical power for patients and caregivers can be reduced. This is achieved by the arrangement that fluid having a higher temperature than the first temperature, that is the temperature of the treatment fluid while dialysis treatment is being performed, is conveyed from the Tank 150 in order to provide treatment fluid substantially at the first temperature at a time when the dialysis monitor has detected that externally provided electrical power to the dialysis monitor has been interrupted.

Assuming the hot fluid in the Tank 150 has a temperature of 90° C., and the set temperature of the treatment fluid to be used by the Dialysis Monitor during dialysis treatment of a patient is 37° C., then Formula 1 applies:

$$V_{Tank}*(90-37)=V_{Inlet}*(37-T_{Inlet}) \quad \text{(Formula 1)}$$

where $V_{Tank}$ is the volume of the Tank, $T_{Inlet}$ is the temperature of the fluid entering at the Inlet and $V_{Inlet}$ is the volume of fluid entering at the Inlet. Further assuming the Tank has a volume of 5 liters and the fluid entering the Inlet has a temperature of 20° C. then the volume of fluid entering the Inlet which can be heated to 37° C. by means of the hot fluid in the Tank is given by Formula 2:

$$V_{Inlet}=5*(90-37)/(37-20)=15.6[\text{liters}] \quad \text{(Formula 2)}$$

Further assuming the required volume of fluid for the treatment is approximately 0.5 [liters/minute], the hot fluid of the Tank will be able to heat the incoming water for a period of 31 minutes. It should be noted that interruptions of externally provided electrical power, which may be frequent in many developing countries, in many cases have a duration of less than 30 minutes. This means that the present invention in many cases allows dialysis treatment to be continued without interruption even though externally provided electrical power has been interrupted which, in turn, is to the benefit of patients, clinics/hospitals, and even nurses in reduced (over-time) working-hours.

An advantage, at least in respect of some embodiments of the present invention, is that the time spent on the starting-up of, or preparation of, the treatment fluid before the dialysis treatment can be commenced on the patient can be shortened. This is achieved by the arrangement that fluid having a higher temperature than the first temperature, that is the temperature of the treatment fluid while dialysis treatment is being performed, is conveyed from the tank in order to provide treatment fluid substantially at the first temperature.

Another advantage, at least in respect of some embodiments of the present invention, is that disinfection and/or cleaning fluids which was used at an earlier disinfection and/or cleaning event can be re-used. This is achieved by the arrangement that disinfection and/or cleaning fluid is stored in the tank at the end of or after a first disinfection and/or cleaning event, and that at least a portion of the stored disinfection and/or cleaning fluid is discharged into at least of a portion of the treatment fluid path at a subsequent disinfection and/or cleaning event.

Further embodiments of the present invention are disclosed by the following clauses:

Clause 1. A dialysis monitor (100) comprising:
  a treatment fluid path configured to provide treatment fluid at a first temperature to a dialyzer while dialysis treatment is being performed by the dialysis monitor;
  characterized in that the dialysis monitor further comprises:
  a tank connected to the treatment fluid path;
  a heater configured to heat fluid held by the tank;

an actuator connected between the tank and the treatment fluid path, the actuator being configured to fluidly connect or disconnect the tank from the treatment fluid path; and
a controller operatively connected to the heater and the actuator;
wherein the controller is programmed to perform the steps of i) operating the actuator to fluidly connect the tank with the treatment fluid path thereby enabling fluid to enter the tank, ii) operating the actuator to fluidly disconnect the tank from the treatment fluid path, iii) operating the heater to heat the fluid in the tank to achieve and/or maintain and/or exceed a temperature which is higher than said first temperature when dialysis treatment is being performed.

Clause 2. A dialysis monitor (100) comprising:
a treatment fluid path configured to provide treatment fluid at a first temperature to a dialyzer while dialysis treatment is being performed by the dialysis monitor;
characterized in that the dialysis monitor further comprises:
a tank connected to the treatment fluid path;
an actuator connected between the tank and the treatment fluid path, the actuator being configured to fluidly connect or disconnect the tank from the treatment fluid path; and
a controller operatively connected to the actuator;
wherein the controller is programmed to perform the steps of i) retrieving information whether fluid with a temperature higher than said first temperature is present in the treatment fluid path, ii) operating the actuator to fluidly connect the tank with the treatment fluid path thereby enabling fluid to enter the tank at a time the controller has retrieved information that fluid with a temperature higher than said first temperature is present in the treatment fluid path, iii) operating the actuator to fluidly disconnect the tank from the treatment fluid path when dialysis treatment is being performed.

Clause 3. A dialysis monitor according to clause 1 or clause 2 wherein the controller is further programmed to perform the step of iv) operating the actuator to fluidly connect the tank with the treatment fluid path when dialysis treatment is not being performed thereby discharging at least a portion of the fluid in the tank in order to perform thermal disinfection of at least a portion of the treatment fluid path.

Clause 4. A dialysis monitor according to clause 2 or clause 3, in so far as dependent on clause 2, further comprising
a heater configured to heat fluid held by the tank;
wherein the controller is further programmed to perform the step of operating the heater to heat the fluid in the tank when dialysis treatment is being performed.

Clause 5. A dialysis monitor according to clause 4 wherein the controller is programmed to operating the heater in order to achieve and/or maintain and/or exceed a temperature of the fluid in the tank which is higher than the first temperature.

Clause 6. A dialysis monitor according to any one of clause 1 or clause 3 or clause 4 to clause 5 in so far as dependent on clause 3 wherein the heater is located within the tank.

Clause 7. A dialysis monitor according to any one of the preceding clauses further comprising a second heater configured to heat fluid present in the treatment fluid path and the dialysis monitor is configured to convey fluid heated by the second heater to the tank at a time when dialysis treatment is not being performed.

Clause 8. A dialysis monitor according to any one of the preceding clauses wherein the treatment fluid path comprises a used treatment fluid path configured to receive treatment fluid from the dialyzer when treatment is being performed by the dialysis monitor and convey the received treatment fluid to an exit, and the dialysis monitor further comprises a heat exchanger configured to exchange heat between fluid in the treatment fluid path upstream the dialyzer and fluid in said used treatment fluid path, and the dialysis monitor is configured to convey fluid upstream the dialyzer and which has been heated in the heat exchanger to the tank.

Clause 9. A dialysis monitor according to clause 8 wherein the dialysis monitor is configured to convey fluid heated in the heat exchanger to the tank at a point of time thermal disinfection is performed in said used treatment fluid path.

Clause 10 A dialysis monitor according to any one of the preceding clauses wherein the treatment fluid path comprises a fluid inlet and the dialysis monitor is configured to convey fluid received at the fluid inlet to the tank.

Clause 11. A dialysis monitor according to clause 10 wherein the dialysis monitor is configured to receive hot fluid for thermal disinfection trough the fluid inlet and the dialysis monitor is configured to convey at least a portion of the received hot fluid to the tank.

Clause 12. A dialysis monitor according to any one of the preceding clauses as far as dependent on clause 7, wherein the treatment fluid path further comprises a heating vessel, the heating vessel being configured to hold fluid heated by the second heater, and the heating vessel is in communication with the tank such that fluid is conveyed from the tank to the heating vessel when the amount of fluid present in the tank exceeds a set volume.

Clause 13. A dialysis monitor according to clause 12 wherein the heating vessel further comprises a level sensor connected to the controller and the controller is programmed to determine when the tank has been filled with fluid to said set volume by detecting an increased level by means of the level sensor.

Clause 14. A dialysis monitor according to any one of the preceding clauses in so far as dependent on clause 7 wherein the controller is programmed to control the second heater to further heat the fluid which has been discharged from the tank when performing thermal disinfection of the treatment fluid path.

Clause 15. A dialysis monitor according to any one of the preceding clauses wherein the dialysis monitor is configured to discharge the fluid held in the tank at a time when dialysis treatment is not being performed directly into the treatment fluid path.

Clause 16. A dialysis monitor according to any one of the preceding clauses further comprising a second actuator located at the treatment fluid path downstream of the connection of the treatment fluid path to the tank, and the controller is programmed to control the second actuator to close the second actuator at a time fluid is conveyed to the tank.

Clause 17. A dialysis monitor according to any one of the preceding clauses further comprising a third actuator located at the treatment fluid path upstream of the connection of the treatment fluid path to the tank, and the controller is programmed to control the third actuator to close the third actuator at a time fluid is discharged from the tank to the treatment fluid path.

Clause 18. A dialysis monitor according to any one of the preceding clauses further comprising a first temperature sensing device configured to measure the temperature of the fluid in the tank.

Clause 19. A dialysis monitor according to clause 18, in so far as dependent on clause 1 or clause 3, wherein the controller is programmed to read the temperature of the fluid in the tank as measured by the first temperature sensing device and to control the heater such as to achieve a temperature of fluid in the tank at a second temperature.

Clause 20. A dialysis monitor according to clause 18 or clause 19 wherein the controller is programmed to read the temperature of the fluid in the tank as measured by the first temperature sensor and to compare said read temperature of the fluid in the tank with a third temperature and, if the temperature measured by the first temperature sensor reaches and/or exceeds the third temperature, to provide information to a user interface indicative of whether the temperature of fluid in the tank is sufficiently high in order to perform thermal disinfection of the treatment fluid path by means of the fluid in the tank.

Clause 21. A dialysis monitor according to any one of the preceding clauses wherein the tank further comprises a thermally insulating layer which substantially encompasses the tank.

Clause 22. A dialysis monitor according to any one of the preceding clauses wherein the tank comprises an inner wall and an outer wall and a thermally insulating arrangement between the inner and outer wall.

Clause 23. A dialysis monitor according to clause 22 wherein the space between the inner and outer walls is sealed off and substantially void of matter.

Clause 24. A dialysis monitor according to clause 23 wherein the space between the inner and outer walls is sealed off and substantially present a vacuum.

Clause 25. A dialysis monitor according to any one of the preceding clauses in so far as dependent on clause 1 wherein the controller is programmed to perform the step of operating the heater to heat the fluid in the tank to achieve and/or maintain and/or exceed a temperature which is higher than said first temperature when dialysis treatment is being performed is performed at all times while dialysis treatment is being performed on a patient.

Clause 26. A dialysis monitor according to any one of clause 1 to clause 24 in so far as dependent on clause 2 wherein the controller is programmed to perform the step of operating the actuator to fluidly disconnect the tank from the treatment fluid path when dialysis treatment is being performed is performed at all times while dialysis treatment is being performed on a patient.

Clause 27. A dialysis monitor according to any one of the preceding clauses wherein the controller is further programmed to perform the step of operating the actuator to fluidly connect the tank with the treatment fluid path in order to provide treatment fluid substantially at said first temperature.

Clause 28. A dialysis monitor according to clause 27 further comprising a circuit enabling the controller to detect whether externally provided electrical power to the dialysis monitor is interrupted, and wherein the step of operating the actuator to fluidly connect the tank with the treatment fluid path in order to provide treatment fluid substantially at said first temperature is being performed at a time when the controller has detected that externally electrical power to the dialysis monitor has been interrupted.

Clause 29. A dialysis monitor according to any one of clause 27 or clause 28 wherein the controller is programmed to operating the actuator to fluidly connect the tank with the treatment fluid path in order to provide treatment fluid substantially at said first temperature is being performed at a time when the dialysis monitor is starting up the preparation of treatment fluid.

Clause 30. A dialysis monitor according to clause 29 wherein the controller is further programmed to perform the steps of a) operating the actuator to fluidly connect the tank with the treatment fluid path when dialysis treatment is not being performed thereby discharging a portion of the fluid in the tank in order to perform thermal disinfection of the treatment fluid path, and b) operating the actuator to fluidly disconnect the tank from the treatment fluid path thereby retaining an amount of fluid in the tank after having performed thermal disinfection, and c) operating the actuator to fluidly connect the tank with the treatment fluid path in order to provide the retained amount of fluid in order to at least assist in raising the temperature of the treatment fluid towards said first temperature at the time when the dialysis monitor is starting up the preparation of treatment fluid.

Clause 31. A dialysis monitor according to any one clause 27 to clause 30, wherein the treatment fluid path further comprises a fluid inlet and a fluid mixer, said fluid mixer being arranged to mix fluid from the tank and fluid provided to the dialysis monitor through the fluid inlet in order to provided treatment fluid substantially at said first temperature.

Clause 32. A dialysis monitor according to clause 31 wherein the fluid mixer is a thermostatic mixer.

Clause 33. A dialysis monitor according to clause 31, wherein the fluid mixer comprises an adjustment arrangement, said adjustment arrangement being connected to the controller, and wherein the controller is programmed to operating said adjustment arrangement in order to set the fluid mixing ratio between the mixed fluids.

Clause 34. A dialysis monitor according to clause 32 wherein the controller is programmed to operating said adjustment arrangement in order to adjust the target output temperature of the thermostatic mixer.

Clause 35. A dialysis monitor according to any one of clause 27 to clause 34 further comprising a second temperature sensing device configured to measure the temperature of fluid in the treatment fluid path at a location downstream of the connection of the tank to the treatment fluid path, and wherein the controller is programmed to control the temperature of the treatment fluid to the substantially said first temperature by reading the temperature as measured by the second temperature sensing device, and by controlling said actuator, and thereby the amount of fluid entering the fluid path from the tank, based on said read temperature and said first temperature.

Clause 36. A dialysis monitor according to clause 33 or any one of clause 27 to clause 31 further comprising a second temperature sensing device configured to measure the temperature of fluid in the treatment fluid path at a location downstream of the connection of the tank to the treatment fluid path, wherein the controller is programmed to control the temperature of the treatment fluid to the substantially said first temperature by reading the temperature as measured by the second temperature sensing device, and by controlling said adjustment arrangement, and thereby the mixing ratio of the fluid mixer, based on said read temperature and said first temperature.

Clause 37. A dialysis monitor according to clause 34 or any one of clause 27 to clause 32 further comprising a second temperature sensing device configured to measure the temperature of fluid in the treatment fluid path at a location downstream of the connection of the tank to the treatment fluid path, wherein the controller is programmed to control the temperature of the treatment fluid to the substantially said first temperature by reading the temperature as measured by the second temperature sensing device, and by controlling said adjustment arrangement, and thereby the target temperature of the thermostatic mixer, based on said read temperature and said first temperature.

Clause 38. A dialysis monitor according to any one of the preceding clauses wherein said temperature higher than said first temperature is at least 60° C. or at least 80° C.

Clause 39. A dialysis monitor according to any one of the preceding clauses, in so far as dependent on clause 29, wherein the controller is programmed to operating the actuator to fluidly connect the tank with the treatment fluid path in order to provide treatment fluid substantially at said first temperature is being performed at a time when the dialysis monitor is not performing dialysis treatment on a patient.

Clause 40. A dialysis monitor according to any one of the preceding clauses further comprising a back-up battery, said dialysis monitor being configured to provide power to at least a portion of the dialysis monitor from said back-up battery when externally provided electrical power to the dialysis monitor is interrupted.

Clause 41. A method of thermally disinfecting at least a portion of a treatment fluid path of a dialysis monitor, the dialysis monitor having a treatment fluid path configured to provide treatment fluid at a first temperature to a dialyzer while dialysis treatment is being performed by the dialysis monitor, a tank connected to the treatment fluid path, a heater configured to heat fluid held by the tank, an actuator connected between the tank and the treatment fluid path, the actuator being configured to fluidly connect or disconnect the tank from the treatment fluid path, the method comprising the steps of:
  i) operating the actuator to fluidly connect the tank with the treatment fluid path thereby enabling fluid to enter the tank;
  ii) operating the actuator to fluidly disconnect the tank from the treatment fluid path;
  iii) operating the heater to heat the fluid in the tank to achieve and/or maintain, and/or exceed a temperature which is higher than the first temperature when dialysis treatment is being performed; and
  iv) operating the actuator to fluidly connect the tank with the treatment fluid path when dialysis treatment is not being performed thereby discharging the fluid in the tank in order to perform thermal disinfection of the treatment fluid path.

Clause 42. A method of thermally disinfecting at least a portion of a treatment fluid path of a dialysis monitor, the dialysis monitor having a treatment fluid path configured to provide treatment fluid at a first temperature to a dialyzer while dialysis treatment is being performed by the dialysis monitor, a tank connected to the treatment fluid path, an actuator connected between the tank and the treatment fluid path, the actuator being configured to fluidly connect or disconnect the tank from the treatment fluid path, the method comprising the steps of:
  i) operating the actuator to fluidly connect the tank with the treatment fluid path thereby enabling fluid to enter the tank at a time the controller has information that fluid with a temperature higher than the first temperature is present in the treatment fluid path;
  ii) operating the actuator to fluidly disconnect the tank from the treatment fluid path while dialysis treatment is being performed; and
  iii) operating the actuator to fluidly connect the tank with the treatment fluid path when dialysis treatment is not being performed thereby discharging the fluid in the tank in order to perform thermal disinfection of the treatment fluid path.

Clause 43. A method of thermally disinfecting at least a portion of a treatment fluid path of a dialysis monitor according to clause 42 the dialysis monitor further having a heater configured to heat fluid held by the tank, the method further comprises the step of operating the heater to heat the fluid in the tank while dialysis treatment is being performed.

Clause 44. A method of thermally disinfecting at least a portion of a treatment fluid path of a dialysis monitor according to clause 43 wherein the step of operating the heater comprises operating the heater in order to achieve a temperature of the fluid in the tank which is higher than the first temperature.

Clause 45. A method of thermally disinfecting at least a portion of a treatment fluid path of a treatment fluid path according to any one of clause 41 or clause 43 or clause 44, insofar as dependent on clause 41, further comprising the step of
  heating the fluid held in the tank at least during a period of time when the fluid in the tank is fluidly disconnected from the treatment fluid path.

Clause 46. A method of heating treatment fluid of a dialysis monitor, said dialysis monitor being configured to use treatment fluid at a first temperature while dialysis treatment is being performed, a tank connected to the treatment fluid path, an actuator connected between the tank and the treatment fluid path, a heater configured to heat fluid held by the tank, the actuator being configured to fluidly connect or disconnect the tank from the treatment fluid path, the method comprising the step of:
  i) operating the actuator to fluidly connect the tank with the treatment fluid path thereby enabling fluid to enter the tank;
  ii) operating the actuator to fluidly disconnect the tank from the treatment fluid path;
  iii) operating the heater to heat the fluid in the tank to achieve and/or maintain, and/or exceed a temperature which is higher than the first temperature when dialysis treatment is being performed; and
  iv) operating the actuator to fluidly connect the tank with the treatment fluid path so as to maintain said first temperature of the treatment fluid.

Clause 47. A method of heating treatment fluid of a dialysis monitor, said dialysis monitor being configured to use treatment fluid at a first temperature while dialysis treatment is being performed, a tank connected to the treatment fluid path, an actuator connected between the tank and the treatment fluid path, the actuator being configured to fluidly connect or disconnect the tank from the treatment fluid path, the method comprising the step of:
  i) retrieving information whether fluid with a temperature higher than said first temperature is present in the treatment fluid path,
  ii) operating the actuator to fluidly connect the tank with the treatment fluid path thereby enabling fluid to enter the tank at a time the controller has retrieved information that fluid with a temperature higher than said first temperature is present in the treatment fluid path,
  iii) operating the actuator to fluidly disconnect the tank from the treatment fluid path, and iv) operating the actuator to fluidly connect the tank with the treatment fluid path so as to maintain said first temperature of the treatment fluid when dialysis fluid is being prepared at said first temperature.

Clause 48. A method of heating treatment fluid of a dialysis monitor according to any one of clause 46 or clause 47 further comprising the step of detecting whether there is an interruption of externally provided electrical power to the dialysis monitor when dialysis treatment is being performed, and wherein the step of operating the actuator to fluidly connect the tank with the treatment fluid path is performed if it has been detected that the externally electrical power to the dialysis monitor has been interrupted.

Clause 49. A method of heating treatment fluid of a dialysis monitor according to any one of clause 46 or clause 47 wherein operating the actuator to fluidly connect the tank with the treatment fluid path so as to maintain said first temperature of the treatment fluid is performed at a time when the dialysis monitor is starting up the preparation of treatment fluid and the dialysis monitor is not performing dialysis treatment on a patient.

Clause 50. A method of heating treatment fluid according to any one clause 46 to clause 49 wherein said temperature higher than said first temperature is at least 60° C.

Clause 51. A method of heating treatment fluid according to any one of clause 46 to clause 49 wherein said temperature higher than said first temperature is at least 80° C.

Clause 52. A dialysis monitor (100) comprising:
a treatment fluid path configured to provide treatment fluid to a dialyzer while dialysis treatment is being performed by the dialysis monitor;
characterized in that the dialysis monitor further comprises:
a tank connected to the treatment fluid path;
an actuator connected between the tank and the treatment fluid path, the actuator being configured to fluidly connect or disconnect the tank from the treatment fluid path; and
a controller operatively connected to the actuator;
wherein the controller is programmed to perform the steps of i) performing disinfection and/or cleaning of at least a portion of said treatment fluid path by means of a disinfection and/or cleaning fluid at a first disinfection and/or cleaning event, ii) storing at least a portion of said disinfection and/or cleaning fluid in said tank at the end of or after said first disinfection and/or cleaning event, and iii) discharging at least a portion of said stored disinfection and/or cleaning fluid into at least of a portion of said treatment fluid path at a subsequent disinfection and/or cleaning event.

Clause 53. A dialysis monitor according to clause 52 wherein said controller is programmed to arrange that said tank holds said stored disinfection and/or cleaning fluid while said treatment fluid path is supplying treatment fluid during a dialysis treatment.

Clause 54. A dialysis monitor according to any one of clause 52 or clause 53 wherein said controller is programmed to discharge at least a portion of said disinfection and/or cleaning fluid held in the tank at a time when dialysis treatment is not being performed in order to perform disinfection and or cleaning of at least a portion of said treatment fluid path.

Clause 55. A dialysis monitor according to any one of clause 52 to clause 54 wherein said disinfection and/or cleaning of at least a portion of said treatment fluid path is performed by thermal disinfection and/or cleaning.

Clause 56. A dialysis monitor according to clause 55 wherein the dialysis monitor further comprises a heater configured to heat fluid held by the tank to a temperature enabling thermal disinfection and/or cleaning of said portion of said treatment fluid path when discharged into said portion of said treatment fluid path.

Clause 57. A dialysis monitor according to clause 56 wherein the controller is programmed to control said heater to heat fluid in the tank to said temperature enabling thermal disinfection and/or cleaning.

Clause 58. A dialysis monitor according to any one of clause 56 or clause 57 wherein the heater is located within the tank.

Clause 59. A dialysis monitor according to any one of clause 52 to clause 58 wherein said dialysis monitor is configured to introduce a disinfectant and/or cleaning agent into said disinfection and/or cleaning fluid.

Clause 60. A dialysis monitor according to any one of clause 52 to clause 59 further comprising a second actuator located at the treatment fluid path downstream of the connection of the treatment fluid path to the tank, and the controller is programmed to control the second actuator to close the second actuator at a time fluid is conveyed to the tank.

Clause 61. A dialysis monitor according to any one of clause 52 to clause 60 further comprising a third actuator located at the treatment fluid path upstream of the connection of the treatment fluid path to the tank, and the controller is programmed to control the third actuator to close the third actuator at a time fluid is discharged from the tank to the treatment fluid path.

Yet further embodiments of the present invention are disclosed by the following aspects:

Aspect 1. A dialysis monitor comprising:
a treatment fluid path configured to provide treatment fluid at a first temperature to a dialyzer while dialysis treatment is being performed by the dialysis monitor;
a controller;
characterized in that:
the dialysis monitor further comprises a tank connected to the treatment fluid path; and
the tank being configured to hold a fluid having a temperature higher than said first temperature;
wherein said controller is programmed to arrange that said tank holds said fluid having said higher temperature at least for a period of time when said treatment fluid path is supplying treatment fluid at said first temperature during a dialysis treatment.

Aspect 2. A dialysis monitor according to aspect 1 wherein the dialysis monitor is configured to discharge the fluid held in the tank at a time when dialysis treatment is not being performed in order to perform thermal disinfection of at least a portion of said treatment fluid path.

Aspect 3. A dialysis monitor according to any one of aspect 1 or aspect 2 further comprising a heater configured to heat fluid held by the tank wherein the heater is configured to heat fluid in the tank to achieve and/or maintain and/or exceed said higher temperature.

Aspect 4. A dialysis monitor according to aspect 3 wherein the controller is programmed to control the heater to heat fluid in the tank to achieve and/or maintain and/or exceed said higher temperature.

Aspect 5. A dialysis monitor according to any one of aspect 3 or aspect 4 wherein the heater is located within the tank.

Aspect 6. A dialysis monitor according to any one of the preceding aspects further comprising a second heater configured to heat fluid present in the treatment fluid path and the dialysis monitor is configured to convey fluid heated by the second heater to the tank at a time when dialysis treatment is not being performed.

Aspect 7. A dialysis monitor according to any one of the preceding aspects wherein the treatment fluid path is configured to enable a circulation loop to be formed, within which at least a portion of the fluid present in the treatment fluid path upstream the dialyzer can be circulated, and the dialysis monitor is configured to convey fluid from the circulation loop to the tank.

Aspect 8. A dialysis monitor according to any one of the preceding aspects wherein the treatment fluid path comprises a used treatment fluid path configured to receive treatment fluid from the dialyzer when treatment is being performed by the dialysis monitor and convey the received treatment fluid to an exit, and the dialysis monitor further comprises a heat exchanger configured to exchange heat between fluid in the treatment fluid path upstream the dialyzer and fluid in said used treatment fluid path, and the dialysis monitor is configured to convey fluid upstream the dialyzer which has been heated in the heat exchanger to the tank.

Aspect 9. A dialysis monitor according to aspect 8 wherein the dialysis monitor is configured to convey fluid heated in the heat exchanger to the tank at a point of time thermal disinfection is being performed in said used treatment fluid path.

Aspect 10. A dialysis monitor according to any one of the preceding aspects wherein the treatment fluid path comprises a fluid inlet and the dialysis monitor is configured to convey fluid received at the fluid inlet to the tank.

Aspect 11. A dialysis monitor according to aspect 10 wherein the dialysis monitor is configured to receive hot fluid for thermal disinfection through the fluid inlet and the dialysis monitor is configured to convey at least a portion of the received hot fluid to the tank.

Aspect 12. A dialysis monitor according to any one of the preceding aspects in so far as dependent on aspect 6, wherein the treatment fluid path further comprises a heating vessel, the heating vessel being configured to hold fluid heated by the second heater, and the heating vessel is in communication with the tank such that fluid is conveyed from the tank to the heating vessel when the amount of fluid present in the tank exceeds a set volume.

Aspect 13. A dialysis monitor according to aspect 12 wherein the heating vessel further comprises a level sensor and the dialysis monitor is configured to determine when the tank has been filled with fluid to said set volume by detecting an increased level by means of the level sensor.

Aspect 14. A dialysis monitor according to any one aspect 2 to aspect 13 in so far as dependent on aspect 6 wherein the dialysis monitor is configured to further heat the fluid which has been discharged from the tank when performing thermal disinfection of the treatment fluid path by means of the second heater.

Aspect 15. A dialysis monitor according to any one of aspect 2 to aspect 14 wherein the dialysis monitor is configured to discharge the fluid held in the tank at a time when dialysis treatment is not being performed directly into the treatment fluid path.

Aspect 16. A dialysis monitor according to any one of the preceding aspects further comprising a first actuator located between the tank and the treatment fluid path and configured to fluidly connect and disconnect the tank from the treatment fluid path, and the controller is programmed to control the first actuator to connect the tank to the treatment fluid path when fluid is conveyed to the tank and disconnect the tank from the treatment fluid path when fluid is held in the tank.

Aspect 17. A dialysis monitor according to any one of the preceding aspects further comprising a second actuator located at the treatment fluid path downstream of the connection of the treatment fluid path to the tank, and the controller is programmed to control the second actuator to close the second actuator at a time fluid is conveyed to the tank.

Aspect 18. A dialysis monitor according to any one of the preceding aspects further comprising a third actuator located at the treatment fluid path upstream of the connection of the treatment fluid path to the tank, and the controller is programmed to control the third actuator to close the third actuator at a time fluid is discharged from the tank to the treatment fluid path.

Aspect 19. A dialysis monitor according to any one of the preceding aspects further comprising a first temperature sensing device configured to measure the temperature of the fluid in the tank.

Aspect 20. A dialysis monitor according to aspect 19, in so far as dependent on aspect 3 or aspect 4, wherein the controller is programmed to read the temperature of the fluid in the tank as measured by the first temperature sensing device and to control the heater such as to achieve a temperature of fluid in the tank at a second temperature.

Aspect 21. A dialysis monitor according to any one of aspect 19 or aspect 20 wherein the controller is programmed to read the temperature of the fluid in the tank as measured by the first temperature sensing device and to compare said read temperature of the fluid in the tank with a third temperature and, if the temperature measured by the first temperature sensing device reaches and/or exceeds the third temperature, to provide information to a user interface indicative of whether the temperature of fluid in the tank is sufficiently high in order to perform thermal disinfection of the treatment fluid path by means of the fluid in the tank.

Aspect 22. A dialysis monitor according to any one of the preceding aspects wherein the tank further comprises a thermally insulating layer which substantially encompasses the tank.

Aspect 23. A dialysis monitor according to any one of the preceding aspects wherein the tank comprises an inner wall and an outer wall and a thermally insulating arrangement between the inner and outer wall.

Aspect 24. A dialysis monitor according to aspect 23 wherein the space between the inner and outer walls is sealed off and substantially void of matter.

Aspect 25. A dialysis monitor according to aspect 24 wherein the space between the inner and outer walls is sealed off and substantially present a vacuum.

Aspect 26. A dialysis monitor according to any one of the preceding aspects wherein the dialysis monitor is configured to convey fluid from the tank in order to provide treatment fluid substantially at said first temperature.

Aspect 27. A dialysis monitor according to aspect 26 further comprising a circuit enabling the controller to detect whether externally provided electrical power to the dialysis monitor is interrupted, and wherein the dialysis monitor is configured to convey fluid from the tank at a time when the controller has detected that externally electrical power to the dialysis monitor has been interrupted.

Aspect 28. A dialysis monitor according to any one of aspect 26 or aspect 27 wherein the dialysis monitor is configured to convey fluid from the tank at a time when the dialysis monitor is starting up the preparation of treatment fluid.

Aspect 29. A dialysis monitor according to aspect 28 wherein the dialysis monitor is configured to discharge fluid held in the tank at a time when dialysis treatment is not being performed in order to perform thermal disinfection, and wherein the dialysis monitor is configured to retain an amount of fluid in the tank after having performed thermal disinfection, and wherein the dialysis monitor is configured to convey fluid of said retained amount of fluid from the tank at said time when the dialysis monitor is starting up the preparation of treatment fluid.

Aspect 30. A dialysis monitor according to any one aspect 26 to aspect 29, wherein the treatment fluid path further comprises a fluid inlet and a fluid mixer, said fluid mixer being arranged to mix fluid from the tank and fluid provided to the dialysis monitor through the fluid inlet in order to provided treatment fluid substantially at said first temperature.

Aspect 31. A dialysis monitor according to aspect 30 wherein the fluid mixer is a thermostatic mixer.

Aspect 32. A dialysis monitor according to any one of aspect 30, wherein the fluid mixer comprises an adjustment arrangement, said adjustment arrangement being connected to the controller, and said adjustment arrangement being configured to enable the controller to set the fluid mixing ratio between the mixed fluids.

Aspect 33. A dialysis monitor according to aspect 31 wherein the adjustment arrangement is configured to enable the controller to adjust the target output temperature of the thermostatic mixer.

Aspect 34. A dialysis monitor according to any one of aspect 26 to aspect 33, in so far as dependent on aspect 16, further comprising a second temperature sensor configured to measure the temperature of fluid in the treatment fluid path at a location downstream of the connection of the tank to the treatment fluid path, and wherein the controller is programmed to control the temperature of the treatment fluid to the substantially said first temperature by reading the temperature as measured by the second temperature sensor, and by controlling said first actuator, and thereby the amount of fluid entering the fluid path from the tank, based on said read temperature and said first temperature.

Aspect 35. A dialysis monitor according to aspect 32 further comprising a second temperature sensor configured to measure the temperature of fluid in the treatment fluid path at a location downstream of the connection of the tank to the treatment fluid path, wherein the controller is programmed to control the temperature of the treatment fluid to the substantially said first temperature by reading the temperature as measured by the second temperature sensor, and by controlling said adjustment arrangement, and thereby the mixing ratio of the fluid mixer, based on said read temperature and said first temperature.

Aspect 36. A dialysis monitor according to aspect 33 further comprising a second temperature sensor configured to measure the temperature of fluid in the treatment fluid path at a location downstream of the connection of the tank to the treatment fluid path, wherein the controller is programmed to control the temperature of the treatment fluid to the substantially said first temperature by reading the temperature as measured by the second temperature sensor, and by controlling said adjustment arrangement, and thereby the target temperature of the thermostatic mixer, based on said read temperature and said first temperature.

Aspect 37. A dialysis monitor according to any one of the preceding aspects wherein said temperature higher than said first temperature is at least 60° C. or at least 80° C.

Aspect 38. A dialysis monitor according to any one of the preceding aspects, in so far as dependent on aspect 28 wherein the dialysis monitor is configured to convey fluid from the tank only at a time when dialysis treatment is not being performed on a patient.

Aspect 39. A dialysis monitor according to any one of the preceding aspects further comprising a back-up battery, said dialysis monitor being configured to provide power to at least a portion of the dialysis monitor from said back-up battery when externally provided electrical power to the dialysis monitor is interrupted.

Aspect 40. A method of thermally disinfecting at least a portion of a treatment fluid path of a dialysis monitor at a time when dialysis treatment is not being performed, said dialysis monitor being configured to use treatment fluid at a first temperature while dialysis treatment is being performed, said method comprising the step of:
discharging a preheated fluid from a tank of said dialysis monitor so as to thermally disinfect said at least portion of the treatment fluid path, said discharged fluid having a temperature which is higher than said first temperature;
wherein said discharged fluid was held at a temperature higher than the first temperature at least for a period of time while dialysis treatment was being performed.

Aspect 41. A method of disinfecting a treatment fluid path according to aspect 40 further comprising the step of
heating the fluid held in the tank at least during a period of time when the fluid in the tank is fluidly disconnected from the treatment fluid path and dialysis treatment is being performed.

Aspect 42. A method of disinfecting a treatment fluid path according to any one of aspect 40 or aspect 41 further comprising the steps of:
measuring the temperature of the fluid held in the tank; and
controlling the heating of the fluid held in the tank based on the measured temperature in order to achieve and/or maintain and/or exceed a temperature of the fluid held in the tank which is higher than said first temperature.

Aspect 43. A method of disinfecting a treatment fluid path according to any one of aspect 40 to aspect 42 wherein said temperature higher than said first temperature is at least 60° C. or at least 80° C.

Aspect 44. A method of heating treatment fluid of a dialysis monitor, said dialysis monitor being configured to use treatment fluid at a first temperature while dialysis treatment is being performed and said dialysis monitor comprising a tank, said method comprising the step of:
conveying a preheated fluid from said tank of said dialysis monitor so as to heat the treatment fluid, said preheated fluid having a temperature which is higher than said first temperature;
wherein said conveyed fluid was held at a temperature higher than the first temperature at least for a period of time while dialysis treatment was being performed.

Aspect 45. A method of heating treatment fluid according to aspect 44 further comprising the steps of:
detecting whether there is an interruption of externally provided electrical power to the dialysis monitor; and
conveying the preheated fluid from said tank in order to provide treatment fluid substantially at said first temperature if it has been detected that the externally electrical power to the dialysis monitor has been interrupted.

Aspect 46. A method of heating treatment fluid according to any one of aspect 44 or aspect 45 further comprising the step of:

conveying fluid from the tank at a time when the dialysis monitor is starting up the preparation of treatment fluid and the dialysis monitor is not performing dialysis treatment on a patient.

Aspect 47. A method of heating treatment fluid according to any one aspect 44 to aspect 46 wherein said temperature higher than said first temperature is at least 60° C. or at least 80° C.

Aspect 48. A dialysis monitor comprising:
a treatment fluid path configured to provide treatment fluid to a dialyzer while dialysis treatment is being performed by the dialysis monitor;
a controller;
characterized in that:
the dialysis monitor further comprises a tank connected to the treatment fluid path; and
the dialysis monitor is configured to perform disinfection and/or cleaning of at least a portion of said treatment fluid path by means of a disinfection and/or cleaning fluid at a first disinfection and/or cleaning event; and
the dialysis monitor is configured to store at least a portion of said disinfection and/or cleaning fluid in said tank at the end of or after said first disinfection and/or cleaning event; and
the dialysis monitor is configured to discharge at least a portion of said stored disinfection and/or cleaning fluid into at least of a portion of said treatment fluid path at a subsequent disinfection and/or cleaning event.

Aspect 49. A dialysis monitor according to aspect 48 wherein said controller is programmed to arrange that said tank holds said stored disinfection and/or cleaning fluid at least for a period of time while said treatment fluid path is supplying treatment fluid during a dialysis treatment.

Aspect 50. A dialysis monitor according to any one of aspect 48 or aspect 49 wherein the dialysis monitor is configured to discharge at least a portion of said disinfection and/or cleaning fluid held in the tank at a time when dialysis treatment is not being performed in order to perform disinfection and or cleaning of at least a portion of said treatment fluid path.

Aspect 51. A dialysis monitor according to any one of aspect 48 to aspect 50 wherein said disinfection and/or cleaning of at least a portion of said treatment fluid path is performed by thermal disinfection and/or cleaning.

Aspect 52. A dialysis monitor according to aspect 51 wherein the dialysis monitor further comprises a heater configured to heat fluid held by the tank to a temperature enabling thermal disinfection and/or cleaning of said portion of said treatment fluid path when discharged into said portion of said treatment fluid path.

Aspect 53. A dialysis monitor according to aspect 52 wherein the controller is programmed to control said heater to heat fluid in the tank to said temperature enabling thermal disinfection and/or cleaning.

Aspect 54. A dialysis monitor according to any one of aspect 52 or aspect 53 wherein the heater is located within the tank.

Aspect 55. A dialysis monitor according to any one of aspect 48 to aspect 54 wherein said dialysis monitor is configured to introduce a disinfectant and/or cleaning agent into said disinfection and/or cleaning fluid.

Aspect 56. A dialysis monitor according to any one of aspect 48 to aspect 55 further comprising a first actuator located between the tank and the treatment fluid path and configured to fluidly connect and disconnect the tank from the treatment fluid path, and the controller is programmed to control the first actuator to connect the tank to the treatment fluid path when fluid is conveyed to the tank and disconnect the tank from the treatment fluid path when fluid is held in the tank.

Aspect 57. A dialysis monitor according to any one of aspect 48 to aspect 56 further comprising a second actuator located at the treatment fluid path downstream of the connection of the treatment fluid path to the tank, and the controller is programmed to control the second actuator to close the second actuator at a time fluid is conveyed to the tank.

Aspect 58. A dialysis monitor according to any one of aspect 48 to aspect 57 further comprising a third actuator located at the treatment fluid path upstream of the connection of the treatment fluid path to the tank, and the controller is programmed to control the third actuator to close the third actuator at a time fluid is discharged from the tank to the treatment fluid path.

Aspect 59. A method of disinfecting and/or cleaning at least a portion of a treatment fluid path of a dialysis monitor at first and subsequent events when dialysis treatment is not being performed, said method comprising the steps of:
disinfecting and/or cleaning at least a portion of said treatment fluid path at said first disinfection and/or cleaning event by means of a disinfection and/or cleaning fluid; and
storing at least a portion of said disinfection and/or cleaning fluid in a tank at the end of or after said first disinfection and/or cleaning event; and
discharging at least a portion of said stored disinfection and/or cleaning fluid into at least of a portion of said treatment fluid path at a subsequent disinfection and/or cleaning event.

Aspect 60. A method of disinfecting and/or cleaning at least a portion of a treatment fluid path according to aspect 59 further comprising the steps of:
arranging that said tank holds said stored disinfection and/or cleaning fluid at least for a period of time while said treatment fluid path is supplying treatment fluid during a dialysis treatment.

Aspect 61. A method of disinfecting and/or cleaning at least a portion of a treatment fluid path according to any one of aspect 59 or aspect 60 further comprising the step of:
heating said stored disinfection and/or cleaning fluid and performing thermal disinfection and/or cleaning at said subsequent disinfection and/or cleaning event.

Aspect 62. A method of disinfecting and/or cleaning at least a portion of a treatment fluid path according to any one of aspect 59 to aspect 61 further comprising the step of:
introducing a disinfectant and/or cleaning agent into said disinfection and/or cleaning fluid.

The invention claimed is:

1. A dialysis monitor configured to be coupled to a disposable extracorporeal blood circuit, the dialysis monitor comprising:
an inlet configured for receiving purified water from a water supply system located external to the dialysis monitor;
a treatment fluid path configured to provide treatment fluid at a first temperature to a dialyzer while dialysis treatment is being performed, wherein the treatment fluid path includes an inlet valve connected to the inlet;
a tank located within the dialysis monitor and connected to the treatment fluid path, the tank configured to hold a fluid having a temperature higher than said first temperature; and
a controller programmed to (i) arrange that said tank holds said fluid having said higher temperature at least for a period of time when said treatment fluid path is supplying treatment fluid at said first temperature during the dialysis treatment, (ii) cause the fluid held in the tank to be discharged at a time when dialysis treatment is not being performed in order to perform thermal disinfection of at least a portion of said treatment fluid path, and (iii) set the inlet valve in a fluidly closed state at the time of the thermal disinfection.

2. The dialysis monitor according to claim 1, further comprising a heater configured to heat fluid held by the tank to achieve and/or maintain and/or exceed said higher temperature.

3. The dialysis monitor according to claim 1, the dialysis monitor is configured to convey the water received at the inlet to the tank.

4. The dialysis monitor according to claim 3, which is configured to receive the fluid for thermal disinfection through the inlet and convey at least a portion of the received fluid to the tank.

5. The dialysis monitor according to claim 1, further comprising a first actuator located between the tank and the treatment fluid path and configured to fluidly connect and disconnect the tank from the treatment fluid path, and wherein the controller is programmed to control the first actuator to connect the tank to the treatment fluid path when fluid is conveyed to the tank and disconnect the tank from the treatment fluid path when fluid is held in the tank.

6. The dialysis monitor according to claim 5, further comprising a second actuator located at the treatment fluid path downstream of the connection of the treatment fluid path to the tank, and the controller is programmed to control the second actuator to close the second actuator at a time fluid is conveyed to the tank.

7. The dialysis monitor according to claim 1, which is configured to convey fluid from the tank to provide treatment fluid substantially at said first temperature.

8. The dialysis monitor according to claim 7, further comprising a circuit enabling the controller to detect whether externally provided electrical power to the dialysis monitor is interrupted, and wherein the dialysis monitor is configured to convey fluid from the tank at a time when the controller has detected that externally electrical power to the dialysis monitor has been interrupted.

9. The dialysis monitor according to claim 7, which is configured to convey fluid from the tank at a time when the dialysis monitor is starting up the preparation of treatment fluid.

10. The dialysis monitor according to claim 9, which is configured to (i) retain an amount of fluid in the tank after having performed thermal disinfection, and (ii) convey fluid of said retained amount of fluid from the tank at said time when the dialysis monitor is starting up the preparation of treatment fluid.

11. The dialysis monitor according to claim 7, wherein the treatment fluid path further comprises a fluid mixer, said fluid mixer arranged to mix fluid from the tank and fluid provided to the dialysis monitor through the inlet to provide treatment fluid substantially at said first temperature.

12. The dialysis monitor according to claim 1, which includes:
a treatment fluid pump;
wherein the treatment fluid pump pumps the treatment fluid at the first temperature through the treatment fluid path to the dialyzer.

13. A method of thermally disinfecting at least a portion of a treatment fluid path of a dialysis monitor at a time when dialysis treatment is not being performed, said dialysis monitor configured to be coupled to a disposable extracorporeal blood circuit and to use treatment fluid at a first temperature while dialysis treatment is being performed, said method comprising:
receiving purified water from a water supply system located external to the dialysis monitor, through an inlet of the dialysis monitor, into a tank located within the dialysis monitor, the tank being in fluid communication with the treatment fluid path;
storing the water in the tank as preheated fluid; and
discharging the preheated fluid from the tank of said dialysis monitor so as to thermally disinfect said at least a portion of the treatment fluid path, said discharged fluid having a temperature which is higher than said first temperature,
wherein said preheated fluid stored in the tank is maintained above the first temperature at least for a period of time while dialysis treatment is performed.

14. The method of claim 13, further comprising:
heating the fluid held in the tank at least during a period of time when the fluid in the tank is fluidly disconnected from the treatment fluid path and dialysis treatment is being performed.

15. The method according to claim 13, wherein the dialysis monitor includes a treatment fluid pump to pump the treatment fluid at the first temperature through the treatment fluid path to a dialyzer.

16. A method of heating treatment fluid of a dialysis monitor, said dialysis monitor configured to use treatment fluid at a first temperature while dialysis treatment is performed, said dialysis monitor configured to be coupled to a disposable extracorporeal blood circuit and comprising a tank in fluid communication with a treatment fluid path, said method comprising:
receiving purified water from a water supply system located external to the dialysis monitor, through an inlet of the dialysis monitor, into the tank located within the dialysis monitor;
storing the water in the tank as preheated fluid; and
conveying the preheated fluid from said tank of said dialysis monitor so as to heat the treatment fluid, said preheated fluid having a temperature which is higher than said first temperature,
wherein said preheated fluid stored in the tank is maintained above the first temperature at least for a period of time while dialysis treatment is performed.

17. The method of heating treatment fluid according to claim 16, further comprising:
detecting whether there is an interruption of externally provided electrical power to the dialysis monitor; and
conveying the preheated fluid from said tank to provide treatment fluid substantially at said first temperature upon detecting that the externally provided electrical power to the dialysis monitor has been interrupted.

18. The method of heating treatment fluid according to claim 16, further comprising:
conveying fluid from the tank at a time when the dialysis monitor is starting up the preparation of treatment fluid and the dialysis monitor is not performing dialysis treatment on a patient.

19. The method according to claim 16, wherein the dialysis monitor includes a treatment fluid pump to pump the treatment fluid at the first temperature through a treatment fluid path to a dialyzer.

20. A dialysis monitor configured to be coupled to a disposable extracorporeal blood circuit, the dialysis monitor comprising:

an inlet configured for receiving purified water from a water supply system located external to the dialysis monitor;

a treatment fluid path configured to provide treatment fluid to a dialyzer while dialysis treatment is being performed, wherein the treatment fluid path includes an inlet valve connected to the inlet;

a tank located within the dialysis monitor, connected to the treatment fluid path and configured to store at least a portion of the water received through the inlet for use as disinfection and/or cleaning fluid; and a controller configured to (i) perform disinfection and/or cleaning of at least a portion of said treatment fluid path by means of the disinfection and/or cleaning fluid at a first disinfection and/or cleaning event, (ii) store at least a portion of said disinfection and/or cleaning fluid in said tank at the end of or after said first disinfection and/or cleaning event, and (iii) discharge at least a portion of said stored disinfection and/or cleaning fluid into at least a portion of said treatment fluid path at a subsequent disinfection and/or cleaning event.

21. The dialysis monitor according to claim 20, wherein said controller is programmed to arrange that said tank holds said stored disinfection and/or cleaning fluid at least for a period of time while said treatment fluid path is supplying treatment fluid during a dialysis treatment.

22. The dialysis monitor according to claim 20, which includes:

a treatment fluid pump;

wherein the treatment fluid pump pumps the treatment fluid through the treatment fluid path to the dialyzer.

23. A method of disinfecting and/or cleaning at least a portion of a treatment fluid path of a dialysis monitor at first and subsequent events when dialysis treatment is not being performed, the dialysis monitor configured to be coupled to a disposable extracorporeal blood circuit and including an inlet configured for receiving purified water from a water supply system located external to the dialysis monitor, and further including a tank located within the dialysis monitor and configured to store at least a portion of the water received through the inlet for use as disinfection and/or cleaning fluid, said method comprising:

disinfecting and/or cleaning at least a portion of said treatment fluid path at a first disinfection and/or cleaning event by means of the disinfection and/or cleaning fluid;

storing at least a portion of said disinfection and/or cleaning fluid in a tank at the end of or after said first disinfection and/or cleaning event; and discharging at least a portion of said stored disinfection and/or cleaning fluid into at least a portion of said treatment fluid path at a subsequent disinfection and/or cleaning event.

24. The method of claim 23, further comprising:

arranging said tank to hold said stored disinfection and/or cleaning fluid at least for a period of time while said treatment fluid path is supplying treatment fluid during a dialysis treatment.

25. The method according to claim 23, wherein the dialysis monitor includes a treatment fluid pump to pump treatment fluid through the treatment fluid path to a dialyzer.

* * * * *